United States Patent [19]
Harley et al.

[11] Patent Number: 5,863,726
[45] Date of Patent: *Jan. 26, 1999

[54] TELOMERASE ACTIVITY ASSAYS

[75] Inventors: Calvin Bruce Harley, Palo Alto; Nam Woo Kim, San Jose; Scott Lawrence Weinrich, Redwood City, all of Calif.

[73] Assignee: Geron Corporation, Menlo Park, Calif.

[*] Notice: The term of this patent shall not extend beyond the expiration date of Pat. No. 5,629,154.

[21] Appl. No.: 631,554

[22] Filed: Apr. 12, 1996

Related U.S. Application Data

[63] Continuation-in-part of Ser. No. 482,132, Jun. 7, 1995, which is a continuation-in-part of Ser. No. 315,214, Sep. 28, 1994, Pat. No. 5,629,154, which is a continuation-in-part of Ser. No. 255,774, Jun. 7, 1994, which is a continuation-in-part of Ser. No. 151,477, Nov. 12, 1993, and Ser. No. 153,051, Nov. 12, 1993, Pat. No. 5,645,986.

[51] Int. Cl.$^6$ .............................. C12Q 1/68; C07H 21/04; C12P 19/34
[52] U.S. Cl. .......................... 435/6; 435/91.2; 435/91.21; 435/810; 435/183; 435/194; 536/24.31; 536/24.33; 935/8; 935/17; 935/78
[58] Field of Search .............................. 435/6, 91.2, 91.1, 435/183, 184, 91.21, 810; 536/23.1, 24.3, 1, 24.33; 530/300; 935/8, 78, 17

[56] References Cited

U.S. PATENT DOCUMENTS

| | | |
|---|---|---|
| 4,424,279 | 1/1984 | Bohn et al. . |
| 4,737,454 | 4/1988 | Dattagupta . |
| 5,041,199 | 8/1991 | DiFranco . |
| 5,091,302 | 2/1992 | Newman et al. ............................ 435/6 |
| 5,124,246 | 6/1992 | Urdea et al. . |
| 5,137,031 | 8/1992 | Gurguis . |
| 5,188,963 | 2/1993 | Stapleton . |
| 5,196,306 | 3/1993 | Bobrow et al. . |
| 5,231,015 | 7/1993 | Cummins et al. . |
| 5,310,652 | 5/1994 | Gelfand et al. . |
| 5,334,499 | 8/1994 | Burdick et al. . |
| 5,369,003 | 11/1994 | Reischl et al. . |
| 5,413,924 | 5/1995 | Kosak et al. . |
| 5,415,758 | 5/1995 | Comeau . |
| 5,451,500 | 9/1995 | Stapleton . |
| 5,474,916 | 12/1995 | Reishcl et al. . |
| 5,489,508 | 2/1996 | West et al. . |
| 5,491,063 | 2/1996 | Fisher et al. . |
| 5,538,848 | 7/1996 | Livak et al. . |
| 5,545,522 | 8/1996 | Van Gelder et al. ........................ 435/6 |
| 5,639,613 | 6/1997 | Shay et al. . |
| 5,645,986 | 7/1997 | West et al. ................................... 435/6 |
| 5,648,215 | 7/1997 | West et al. ................................... 435/6 |

FOREIGN PATENT DOCUMENTS

| | | |
|---|---|---|
| 2259138 | 3/1993 | United Kingdom . |
| 2294322 | 4/1996 | United Kingdom . |
| 9304546 | 5/1993 | WIPO . |
| WO 93/23572 | 11/1993 | WIPO . |
| 9408053 | 4/1994 | WIPO . |
| WO 95/13381 | 5/1995 | WIPO . |

OTHER PUBLICATIONS

Counter et al. EMBO J. 11: 1921–1929, 1992.
Yu et al. nature 344: 126–132, 1990.
Allsopp et al., "Telomere Length Predicts Replicative Capacity of Human Fibroblasts," *Proc. Natl. Acad. Sci. USA* 89:10114–10118 (1992).
Baird et al., "Mechanism Underlying Telomere Repeat Turnover Revealed by Hypervariable Variant Repeat Distribution Patterns in the Human Xp/Yp Telomere" *EMBO J.* 14:5433–5443 (1995).
Barany, Genetic Disease and DNA Amplifications Using Cloned Thermostable Ligase, *Proc. Natl. Acad. Sci. USA*, 88:189–193 (1991).
Blackburn, "The Molecular Structure of Centromeres and Telemeres" *Annual Reviews in Biochemistry* 53:163 (1984).
Blackburn et al., Recognition and Elongation of Telemeres by Telomerase, Genome, 31:553–560 (1989).
Blackburn, Structure and Function of Telomeres, Nature, 350:569–573 (May 1991).
Cech, "Ribozymes and Their Medical Implications" *JAMA*, 260:3030 (1988).
Cooke and Smith, "Variability at the Telomeres of the Human X/Y Pseudoautosomal Region" *CSHSQB* LI:213 (1986).
Cotten, "The In Vivo Application of Ribosomes," *Trends in Biotechnology* 8:174–178 (1990).
Counter et al., Telomere Shortening Associated with Chromosome Instability is Arrested in Immortal Cells Which Express Telomerase Activity, *The EMBO Journal*, 11(5):1921–1929 (1992).
Counter et al., Telomerase Activity in Human Ovarian Carcinoma, *Proc. Natl. Acad. Sci.*, 91:2900–2904 (Apr. 1994).
Counter et al., Telomerase Activity in Normal Leukocytes and in Hematologic Malignancies, *Blood*, 85(9):2315–2320 (May 1995).
Counter et al., Stabilization of Short Telomeres and Telomerase Activity Accompany Immortalization of Epstein–Barr Virus–Transformed Human B Lymphocytes, Journal of Virology, 68(5):3410–3414 (May 1994).
Eck and Nabel, "Antisense Oligonucleotides for Therapeutic Intervention" *Opin. Biotech* 897 (1991).
Gall, "Tying Up Loose Ends" *Nature* 344:108 (1990).

(List continued on next page.)

*Primary Examiner*—Carla J. Myers
*Attorney, Agent, or Firm*—Melya J. Hughes; Richard L. Neeley; Kevin R. Kaster

[57] ABSTRACT

Telomerase activity in a sample can be measured using a two reaction protocol. The first reaction involves the formation of telomerase substrate extension products from a telomerase substrate. The second reaction involves replication of the telomerase substrate extension products and/or amplification of signal generated by a bound probe. The presence of telomerase activity in a human somatic tissue or cell sample is positively correlated with the presence of cancer and can be used to diagnose a disease or other conditions of medical interest, as well as the course of disease progression or remission in a patient.

44 Claims, 1 Drawing Sheet

OTHER PUBLICATIONS

Goldstein, "Replicative Senescence: The Human Fibroblast Comes of Age" *Science* 249:1129 (1990).

Gottschling et al., "Position Effect at *S. cerevisiae* Telomeres: Reversible Repression of Pol II Transcription" *Cell* 63:751 (1990).

Gray et al., "Cloning and Expression of Genes for the Oxytricha Telomere–binding Protein Specific Subunit Interactions in the Telomeric Complex" *Cell* 67:807 (1991).

Greider, "Telomeres, Telomerase and Senescence" *Bioessays* 12:63 (1990).

Greifer, "Chromosome First Aid" *Cell* 67:645 (1991).

Greider, Telomerase Is Processive, Molecular and Cellular Biology, 11:4572–4580 (Sep. 1991).

Greider and Blackburn, The Telomere Terminal Transferase of Tetrahymena Is a Ribonucleoprotein Enzyme with Two Kinds of Primer Specificity, Cell, 51:887–898 (1987).

Greider et al., Identification of a Specific Telomere Terminal Transferase Activity in Tetrahymena Extracts, *Cell*, 43:405–413 (Dec. 1985).

Greider et al., A Telomeric Sequence in the RNA of Tetrahymena Telomerase Required for Telomere Repeat Synthesis, *Nature*, 337:331–337 (Jan. 1989).

Ham and McKeehan, "Media and Growth Requirements-"*Methods in Enzymology* LVIII:44 (1979).

Harley et al., Telomeres Shorten During Ageing of Human Fibroblasts, *Nature*, 345:458–460 (May 1990).

Harley et al. Telomere Loss: Mitotic Clock or Genetic Time Bomb?, *Mutation Research*, 256:271–282 (1991).

Harley et al., "The Telomere Hypothesis of Cellular Aging," *Experimental Gerontology* 27:375–382 (1992).

Harrington and Greider, "Telomerase Primer Specificity and Chromosome Healing" *Nature* 353:451 (1991).

Hayflick and Moorhead, "The Serial Cultivation of Human Diploid Cell Strains" *Experimental Cell Research* 25:585 (1961).

Henderson et al., "Telomere G–strand Structure and Function Analyzed by Chemical Protection, Base Analogue Substitution, and Utilization by Telomerase In Vitro" *Biochemistry* 29:732 (1990).

Hiyama et al., Length of Telomeric Repeats in Neuroblastoma: Correlation with Prognosis and Other Biological Characteristics, Jpn. J. Cancer Res., 83:159–164 (1992).

Ijdo et al., "Improved Telomere Detection Using a Telomere Repeat Probe (TTAGGG)$_n$ Generated by PCR" *Nucleic Acids Research* 19:4780 (1991).

Innis et al. In PCR Protocols: A Guide to Methods and Applications, Ch. 1, 2 and 3 (1990).

Jankovic et al., "Telomere Loss and Cancer" *Nature* 350:197 (1991).

Kim et al., Specific Association of Human Telomerase Activity with Immortal Cells and Cancer, *Science*, 266:2011–2015 (Dec. 1994).

Klingelhutz et al., "Restoration of Telomeres in Human Papoillomavirus–Immortalized Human Anogenital Epithelial Cells," *Molecular and Cellular Biology* 14:961–969 (1994).

Kwoh et al., "Transcription Based Amplification System and Detection of Amplified Human Immunodeficiency Virus Type 1 with a Bead–Based Sandwich Hybridization Format" *Proc. Natl. Acad. Sci. USA* 86:1173–1177 (1989).

Lundblad and Szostak, "A Mutant With a Defect in Telomere Elogation Leads to Senescence in Yeast" *Cell* 57:633 (1989).

Morin, "Recognition of a Chromosome Truncation Site Associated with Alpha–Thalassaemia by Human Telomerase" *Nature* 353:454–456.

Morin, The Human Telomere Terminal Transferase Enzyme is Ribonucleoprotein That Synthesizes TTAGGG Repeats, *Cell*, 59:521–529 (Nov. 1989).

Müller et al., "New Telomere Formation After Developmentally Regulated Chromosomal Breakage During the Process of Chromosome Diminution in *Ascaris lumbricoides*" *Cell* 67:815 (1991).

Ohno, "Strict Relationship Between Dialyzed Serum Concentration and Cellular Life Span In Vitro" *Mechanisms of Aging and Development* 11:179 (1979).

Olovnikov "A Theory of Marginotomy" *J. Theoretical Biology* 41:181 (1973).

Shay et al., Loss of Telomeric DNA During Aging May Predispose Cells to Cancer, International Journal of Oncology, 3:559–563 (1993).

Smith and Whitney, "Intraclonal Variation in Proliferative Potential of Human Diploid Fibroblastsistochastic Mechanisms for Cellular Aging" *Science* 207:82 (1980).

Starling et al., "Extensive Telomere Repeat Arrays in Mouse are Hypervariable" *Nucleic Acids Research* 18:6881 (1990).

Strahl and Blackburn, "The Effects of Nucleoside Analogs on Telomerase and Telomeres in Tetrahymena" *Nucleic Acids Research* 22:893–900 (1994).

Szostak, "The Beginning of the Ends" *Nature* 337:303 (1989).

Wang and Zaklen, "Telomere–Telomere Recombination Provides an Express Pathway for Telomere Acquisition" *Nature* 345:456 (1990).

Weber et al., "Characterization and Organization of DNA Sequences Adjacent to the Human Telomere Associated Repeat (TTAGGG)$_n$," *Nucleic Acids Research* 18:3353–3361 (1990).

Wilkie et al., "A Truncated Human Chromosome 16 Associated with Alpha Thalassaemia is Stabilized by Addition of Telomeric Repeat (TTAGGG)$_n$," *Abstract, Nature* 346(6287):868–871 (1990).

Windle and McGuire, Telomeres: The Long and the Short of It, Proceedings of the American Association for Cancer Research, Eighty–Third Annual Meeting of the American Association for Cancer Research, 33:594–595 (Mar. 1992).

Yu et al., "In vivo Alternation of Telomere Sequences and Senescences Caused by Mutated Tetrahymena Telomerase RNAs" *Nature* 344:126 (1990).

Yu and Blackburn, "Developmentally Programmed Healing of Chromosomes by Telomerase in Tetrahymena" *Cell* 67:823 (1991).

Zahler et al., "Inhibition of Telomerase by G–quartet DNA Structures" *Nature* 350:718 (1991).

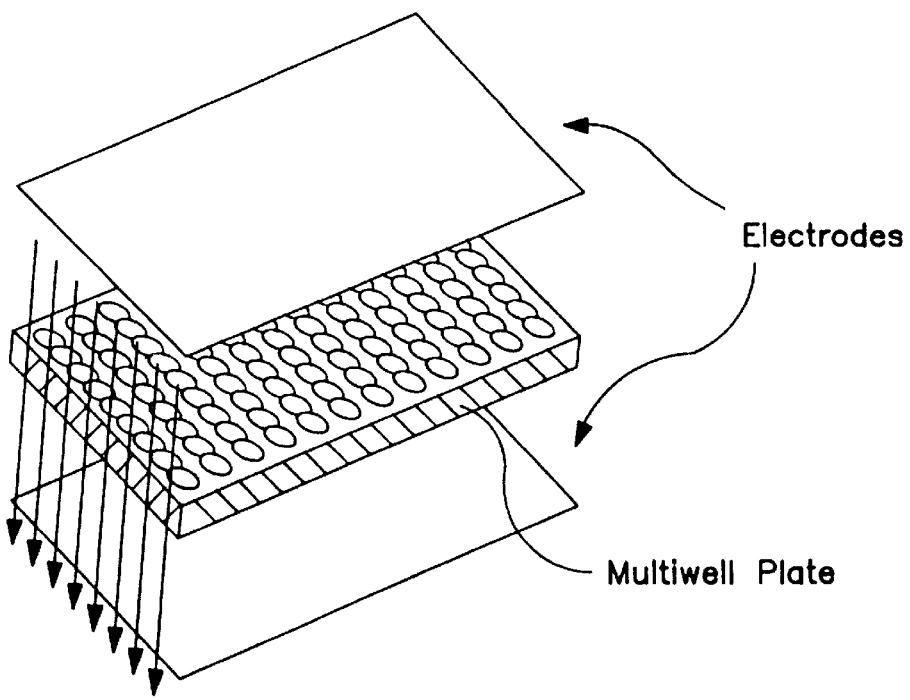
FIG. IA
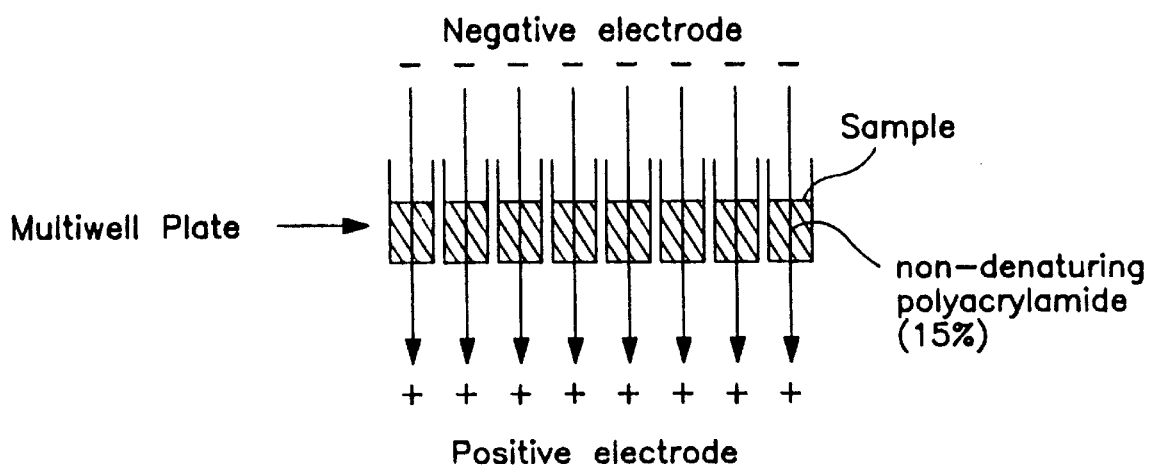
FIG. IB

TELOMERASE ACTIVITY ASSAYS

CROSS-REFERENCE TO RELATED APPLICATIONS

The present application is a continuation-in-part of U.S. patent application Ser. No. 08/482,132, filed Jun. 7, 1995, which is a continuation-in-part of Ser. No. 08/315,214, filed 28 Sep. 1994, now U.S. Pat. No. 5,629,154, which is a continuation-in-part of Ser. No. 08/255,774, filed 7 Jun. 1994, which is a continuation-in-part of Ser. Nos. 08/151,477 and 08/153,051, now U.S. Pat. No. 5,645,986, both of which were filed 12 Nov. 1993. Each of the foregoing patents and patent applications is incorporated herein by reference.

The invention described herein was made with Government support under a grant from the Department of Health and Human Services. The Government has certain rights in this invention.

INTRODUCTION

1. Technical Field

The present invention relates to telomerase, a ribonucleoprotein enzyme involved in telomere DNA synthesis, and provides assays and materials for identifying and measuring telomerase activity. The invention relates to the fields of molecular biology, chemistry, pharmacology, and medical diagnostic and prognostic technology.

2. Background

Telomeres are specialized structures at the ends of eukaryotic chromosomes that function in chromosome stabilization, positioning, and replication (Blackburn and Szostak, 1984, *Ann. Rev. Biochem.* 53:163–194; Zakian, 1989, *Ann. Rev. Genetics* 23:579–604; Blackburn, 1991 *Nature* 350:569–573). In all vertebrates, telomeres consist of hundreds to thousands of tandem repeats of 5'-TTAGGG-3' sequence and associated proteins (Blackburn, 1991; Moyzis et al., 1988, *Proc. Natl. Acad. Sci.* 85:6622–6626). Southern blot analysis of chromosome terminal restriction fragments (TRF) provides the composite lengths of all telomeres in a cell population (Harley et al., 1990, *Nature* 345:458–460; Allsopp et al., 1992, *Proc. Natl. Acad. Sci. USA* 89:10114–10118; Vaziri et al., 1993, *Am. J. Human Genetics* 52:661–667). In all normal somatic cells examined to date, TRF analysis has shown that the chromosomes lose about 50–200 nucleotides of telomeric sequence per cell division, consistent with the inability of DNA polymerase to replicate linear DNA to the ends (Harley et al., 1990; Allsopp et al., 1992; Vaziri et al., 1993; Watson, 1972, *Nature New Biology* 239:197–201).

This shortening of telomeres has been proposed to be the mitotic clock by which cells count their divisions (Harley, 1991, *Mut. Res.* 256:271–282), and a sufficiently short telomere(s) may be the signal for replicative senescence in normal cells (Allsopp et al., 1992; Vaziri et al., 1993; Hastie et al., 1990, *Nature* 346:866–868; Lindsey et al., 1991, *Mut. Res.* 256:45–8; Wright and Shay, 1992, *Trends Genetics* 8:193–197). In contrast, the vast majority of immortal cells examined to date shows no net loss of telomere length or sequence with cell divisions, suggesting that maintenance of telomeres is required for cells to escape from replicative senescence and proliferate indefinitely (Counter et al., 1992, *EMBO* 11:1921–1929; Counter et al., 1994, *Proc. Natl. Acad. Sci. USA* 91:2900–2940).

Telomerase, a unique ribonucleoprotein DNA polymerase, is the only enzyme known to synthesize telomeric DNA at chromosomal ends using as a template a sequence contained within the RNA component of the enzyme (Greider and Blackburn, 1985, *Cell* 43:405–413; Greider and Blackburn, 1989, *Nature* 337:331–337; Yu et al., 1990, *Nature* 344:126–132; Blackburn, 1992, *Ann. Rev. Biochem.* 61:113–129). With regard to human cells and tissues, telomerase activity has been identified in immortal cell lines and in ovarian carcinoma but has not been detected at biologically significant levels (that required to maintain telomere length over many cell divisions) in mortal cell strains or in normal non-germline tissues (Counter et al., 1992; Counter et al, 1994; Morin, 1989, *Cell* 59:521–529). Together with TRP analysis, these results suggest telomerase activity is directly involved in telomere maintenance, lining this enzyme to cell immortality.

Methods for detecting telomerase activity, as well as for identifying compounds that regulate or affect telomerase activity, together with methods for therapy or diagnosis of cellular senescence and immortalization by controlling or measuring telomere length and telomerase activity, have also been described. See PCT patent publication No. 93/23572, published Nov. 25, 1993, and 95/13382, published May 18, 1995, incorporated herein by reference. The identification of compounds affecting telomerase activity provides important benefits to efforts at treating human disease. Compounds that inhibit telomerase activity can be used to treat cancer, as cancer cells express and require telomerase activity for immortality, and most normal human somatic cells do not express telomerase activity. Compounds that stimulate or activate telomerase activity can be used to treat age-related diseases and other conditions relating to cell senescence.

Known methods for assaying telomerase activity in cell samples rely on the incorporation of radioactively labelled nucleotides into a telomerase substrate (Morin, 1989). The conventional assay uses an oligonucleotide substrate, a radioactive deoxyribonucleotide triphosphate (dNTP) for labelling, and gel electrophoresis for resolution and display of products. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists found that reliable telomerase extraction by hypotonic swelling and physical disruption of cells requires at least $10^7$–$10^8$ cells and that the extraction efficiency varies between cell types (Counter et al., 1992; Morin, 1989). There remains a need for telomerase activity assays with increased sensitivity, speed, and efficiency of detecting telomerase activity as compared to the conventional assay, and this invention meets that need.

SUMMARY OF THE INVENTION

It is an object of the invention to provide a readily reproducible assay system for detecting telomerase activity, which is simple enough to use in the smaller (or low budget) clinical setting, but has the potential for high throughput using readily available robotics technology. The assays can be used as diagnostic or prognostic aids, or for the identification, screening, and development of molecules that act as telomerase inhibitors. The present invention also provides reagents, kits, and related methods and materials useful in the practice of the invention.

In one aspect of the invention, a method is provided which comprises the steps of:
(a) incubating a cell sample or an extract derived therefrom in a reaction mixture comprising a telomerase substrate under conditions such that telomerase can catalyze extension of said telomerase substrate by addition of telomeric repeat sequences;
(b) replicating the extended telomerase substrate; and
(c) correlating presence of telomerase activity in the cell sample with presence of the extended telomerase substrate and absence of telomerase activity in the cell sample with absence of the extended telomerase substrate.

In one embodiment, the method involves the extraction of telomerase activity, if any, from a cell sample using, for example, a buffer that comprises a non-ionic and/or a zwitterionic detergent. The extracted telomerase is used to mediate extension of a telomerase substrate in a telomerase substrate extension reaction. Alternatively, the telomerase activity is detected in situ, where a telomerase substrate is internalized by the cells in a sample and then extended by the telomerase in situ.

The extended telomerase substrate can be detected by numerous methods. In one embodiment, the extended telomerase substrate is replicated prior to detection by specific hybridization and subsequent extension of an oligonucleotide "primer" complementary to a telomeric repeat sequence. A number of useful reagents of the invention relate to this step. Typically, primer extension is mediated using a template-dependent DNA polymerase or ligase, and the primer is extended by addition of nucleotides to the primer by the DNA polymerase.

The DNA polymerase used in this step is preferably a thermostable DNA polymerase. Using such a polymerase, one can conduct multiple cycles of primer extension, each cycle comprising the steps of (1) heating the reaction mixture to denature duplex DNA molecules; and (2) cooling the reaction mixture to a temperature at which complementary nucleic acids can hybridize and the polymerase can extend the primer, without inactivating the polymerase. In this embodiment of the method, one can also take advantage of the powerful Polymerase Chain Reaction ("PCR") technology by having an excess amount of the telomerase substrate, which serves as one of the two primers for the PCR, in the reaction mixture and performing the heating and cooling steps 5, 10, 15, 20, 30, or more times. In the PCR embodiment, the telomerase substrate lacks telomeric repeats to minimize primer dimer formation.

Alternatively, the primer extension can be mediated by a template-dependent DNA ligase, so that the primer is extended by addition of an oligodeoxyribonucleotide to the primer by the DNA ligase. Typically, the DNA ligase is a thermostable DNA ligase, and the primer extension step is conducted by (1) heating the reaction mixture to denature duplex DNA molecules; and (2) cooling the reaction mixture to a temperature at which complementary nucleic acids can hybridize and the ligase can extend the primer by ligation. In this embodiment of the method, one can also take advantage of the powerful Ligase Chain Reaction ("LCR") technology by having oligonucleotides ("ligomers") complementary to the extended primer in the reaction mixture and by performing the heating and cooling steps from 5, 10, 15, 20, 30, or more times.

The present invention also provides a number of reagents such as oligonucleotides, primers, and oligomers, useful in the practice of the present invention. For instance, when one is using PCR to amplify a nucleic acid, one needs to avoid nonspecific product formation. Such products can form by a variety of methods, including via interaction of the primers used in the process to form "primer-dimers." The present invention provides primers and reaction conditions designed specifically to minimize the problem of primer-dimer formation. In another aspect, the invention provides primers that limit the size of the largest primer extension product to no more than a defined number of telomeric repeats more than the largest products of telomerase-mediated extension of the telomerase substrate. Control nucleic acids that can be used in a quantitative telomerase assay are also provided.

In a further embodiment, the method detects extended telomerase products by employing RNA polymerase to synthesize multiple RNA copies of the products. In this case, the telomerase extended products contain a promoter sequence that is recognized by the RNA polymerase. Thus, a method is provided which comprises the steps of:
(a) incubating a cell sample or an extract derived therefrom in a reaction mixture comprising a telomerase substrate and a buffer in which telomerase can catalyze extension of the telomerase substrate by addition of telomeric repeat sequences;
(b) adding to the reaction mixture a template-dependent RNA polymerase that recognizes a promoter sequence operably linked to the telomerase substrate under conditions such that the RNA polymerase will form an RNA copy of the extended telomerase substrate if an extended telomerase substrate is present in the reaction mixture; and
(c) correlating presence of telomerase activity in the cell sample with presence of RNA copies of the extended telomerase substrate and absence of telomerase activity in the cell sample with absence of the RNA copies.

In one embodiment, RNA copies of the extended telomerase substrate can be replicated by using reverse transcriptase to make DNA copies of the RNA.

In yet a further aspect of the invention, a method is provided that comprises the steps of:
(a) incubating a cell sample or an extract derived therefrom in a reaction mixture comprising a telomerase substrate and a buffer in which telomerase can catalyze extension of the telomerase substrate by addition of telomeric repeat sequences;
(b) immobilizing the telomerase substrate;
(c) adding to the reaction mixture a probe comprising a sequence sufficiently complementary to the extended telomerase substrate to hybridize specifically thereto under conditions such that if an extended telomerase substrate is present in the reaction mixture, the probe will hybridize to the extended telomerase substrate; and
(d) correlating presence of telomerase activity in the cell sample with presence of the probe hybridized to extended telomerase substrate and absence of telomerase activity in the cell sample with absence of hybridization of the probe.

In a preferred embodiment, signal amplification is achieved by using a branched DNA probe. Such branched DNA probes can be used with or without target nucleic acid amplification.

Irrespective of the replication method, the various reagents can be labelled to facilitate identification and quantitation of telomerase-extended telomerase substrate.

The present invention also provides novel configurations of the reagents useful in the telomerase activity assay and kits comprising those reagents to facilitate practice of the method. A kit comprises a telomerase substrate with or without instructions. A preferred kit comprises the following reagents: CHAPS lysis buffer (10 mM Tris-Cl, pH 7.5; 1 mM MgCl$_2$; 1 mM EGTA; 0.1 mM benzamidine (AEBSF, PMSF or similar reagents can be used in place of or in addition to benzamidine); 5 mM β-mercaptoethanol; 0.5% CHAPS; 10% glycerol), 10×TRAP reaction buffer (200 mM Tris-Cl, pH 8.3; 15 mM MgCl$_2$; 630 mM KCl; 0.05% Tween 20; 10 mM EGTA; 1 mg/ml BSA), 50×dNTP mix (2.5 mM dATP, 2.5 mM dGTP, 2.5 mM dCTP, and 2.5 mM dTTP), TS primer (0.25 μl), water (PCR grade; protease, DNase and RNase-free), positive control cell pellet ($10^6$ cells) or a panel of multiple cell types with varying amounts of telomerase activity, a TRAP primer mix (e.g., ACX 0.1 μg/μl; NT 0.1 μg/μl; TSNT 0.01 amol/μl) and a quantitation standard (e.g., TSR8; 0.1 amol/μl).

In a further aspect of the invention, an assay system and apparatus are provided which allow for high throughput detection of telomerase activity. The assay system and apparatus provide for simultaneous separation of telomerase products from primers and nucleotides in multiple samples and allows for quantitative detection of the isolated telomerase products.

While the methods of the invention are broadly applicable to the detection of telomerase activity in any sample from any origin, the methods are especially useful and applicable to the detection of telomerase activity in samples of biological material obtained from humans. Such samples will contain cells or cellular materials and will typically be obtained from humans for the purpose of detecting a diseased state or other medical condition of interest, such as, cancer. Telomerase is not expressed by most normal postnatal human somatic cells, although low levels of telomerase activity can be detected in certain stem cells, activated cells of the hematopoietic system, and fetal tissues, so the presence of telomerase activity in a sample of human somatic tissue or cells indicates that cells of extended proliferative capacity, such as immortal cells, fetal cells, or hematopoietic cells, are present in the tissue. While not all cancer cells express telomerase activity, telomerase expression is required for cells to become immortal. Consequently, the presence of cells with telomerase activity is associated with many forms of cancer and can also serve to indicate that a particularly invasive or metastatic form of cancer is present.

Thus, the invention provides a method for diagnosis of a condition in a patient associated with an elevated (or reduced) level of telomerase activity within a cell. The method involves determining the presence or amount of telomerase activity within the cells of the patient, and the method is therefore applicable to the detection of elevated (or reduced) levels of telomerase activity associated with, for example, prostate cancer, breast cancer, colon cancer, renal cancer, skin cancer, liver cancer, ovarian cancer, cervical cancer, lung cancer, urogenitary cancer, and leukemia, or, in the case of reduced levels, infertility. The method can also be used for testing other diseased states and medical conditions, e.g., fetal cell testing to detect fetal cells in maternal blood as an indication of pregnancy or to detect telomerase as a marker for bone marrow proliferative capacity. Whether for diagnosis or other purposes, the method involves determining the presence or amount of telomerase activity within the cells by a telomerase substrate extension reaction, and replicating the extended telomerase substrate, for example, by primer extension, such as in the PCR. These and other aspects of the invention will be better understood by reference to the following detailed description of specific embodiments together with the drawings that form part of this specification.

BRIEF DESCRIPTION OF THE DRAWINGS

FIG. 1A is a schematic perspective of the Multiplex Electrophoretic Separator (MES) apparatus of the invention. The parallel arrows depict the direction of the electrical field when the electrodes are attached to the electrical source.

FIG. 1B is a cross sectional view of the MES apparatus.

DESCRIPTION OF SPECIFIC EMBODIMENTS

The present invention provides novel methods and materials for the detection of telomerase activity. Telomerase synthesizes telomeric DNA at the ends of chromosomes and is believed to be necessary for indefinite proliferation of immortal cells. Analysis of chromosome terminal restriction fragments (TRF) in a wide variety of human cell types has shown that telomere length and sequence are stably maintained in immortal cell lines but not in dividing cultures of normal somatic cells. Telomere and telomerase biology are clearly important in the maintenance of the immortal cell state and other biological states.

Thus in one aspect of the invention, a method is provided that involves the basic steps of:

(a) incubating a cell sample or an extract therof in a reaction mixture comprising a telomerase substrate under conditions such that telomerase can catalyze extension of the telomerase substrate by addition of telomeric repeat sequences;

(b) replicating the extended telomerase substrate; and (c) correlating presence of telomerase activity in the cell sample with presence of the extended telomerase substrate.

The method essentially involves two reactions: (1) telomerase-mediated extension of a telomerase substrate; and (2) replication of telomerase-extended substrates. For a more complete understanding of the invention, one should consider certain global issues relating to (1) the nature of the sample; (2) the important features of the telomerase substrate; and (3) the nature of the replication of the telomerase-extended substrate.

Nature of Sample

Any type of sample can be tested by the methods of the invention. Samples of particular interest include cell samples, which can be tissue or tumor samples, obtained for purposes of diagnostic analysis. The expression of telomerase activity in a variety of cells has been studied and discussed in the scientific literature. Telomerase is expressed not only by certain pathogens (i.e., malaria, fungi, yeast, and ciliates) but also by immortal human cells, including certain types of tumor and cancer cells, but is not expressed by cells of normal somatic (as opposed to germline or embryonic) tissue, although low levels of telomerase activity can be detected in stem cells, fetal cells, and in certain activated cells of the hematopoietic system. Consequently, samples can be obtained for the purpose of determining whether a telomerase-expressing pathogen or cancer or tumor cell is present. For such purposes, the sample will often be obtained from a human, but one can also readily understand that samples tested by the present method can be obtained from agriculturally important mammals, such as cattle, horses, sheep, or any other animal of veterinary interest, such as cats and dogs, and from the environment, i.e., for environmental testing for the presence of pathogens.

In one embodiment of the invention, telomerase activity is assayed in vitro, requiring the preparation of a cell extract.

Methods for the preparation of cell extracts are known in the art (for example, see Scopes, 1987, *Protein Purification: Principles and Practice*, Second Edition, Springer-Verlag, N.Y.). Preferably, the detergent lysis method is used which provides more uniform extraction of telomerase even at low cell numbers. The method involves the steps of: (1) collecting a sample of cells; (2) lysing the sample in a lysis buffer comprising 0.01 to 5% of a non-ionic and/or a zwitterionic detergent; (3) removing cellular debris by centrifugation; and (4) collecting supernatant separated from the cellular debris. Such a method is illustrated in Example 1, below. A cell extract can also be prepared merely by lysing a cell sample to release telomerase without further sample preparation.

A wide variety of non-ionic and/or zwitterionic detergents can be employed in the method. Preferred non-ionic detergents include Tween 20, Triton X-100, Triton X-114, Thesit, NP-40, n-octylglucoside, n-dodecylglucoside, n-dodecyl-beta-D-maltoside, octanoyl-N-methylglucamide (MEGA-8), decanoyl-N-methylglucamide (MEGA-10), and isotridecyl-poly(ethyleneglycolether)$_n$, and preferred zwitterionic detergents include CHAPS (3-{(3-cholamidopropyl)dimethylammonio}-1-propane-sulfonate), CHAPSO (3-{(3-cholamidopropyl)dimethyl-ammonio}-2-hydroxy-1-propane-sulfonate), N-dodecyl-N,N-dimethyl-3-ammonio-1-propane-sulfonate, and digitonin, with CHAPS a particularly preferred detergent. While the exact amount of detergent is not critical, 0.5% is typically sufficient to observe the enhanced extraction of telomerase activity.

Although the assay of cell extracts is not limited to extracts that have been obtained using the detergent lysis method, such extracts are preferred, especially when telomerase activity is assayed from a single cell, only a few cells are available or the number of cells expressing telomerase activity in a sample is very low. The telomerase activity assay of the invention is far superior to the conventional assay in detecting telomerase activity in such circumstances, as well as being faster to complete and more efficient.

In another aspect of the invention, the telomerase activity assay is applied to intact cells. In this embodiment, one treats intact cells with the telomerase substrate to promote internalization of the substrate, following which the substrate is extended if the cell possesses functional telomerase activity. Internalization of the substrates can be achieved using methods known in the art, for example, by passive internalization of substrate oligonucleotides or other nucleic acid added to the media surrounding the cell sample (typically at a concentration of 10–100 $\mu$M), by microporation using a detergent or Staphylococcus alpha toxins, by employing liposomes (e.g., LipofectAmine™, Lipofectin™, LipofectAce™ available from BRL), using biolistics, or by electroporation. After the target DNA is internalized by the cell, the sample is incubated to allow any active telomerase present in the cell to extend the substrate by de novo synthesis of telomere repeats. After incubation, the sample is fixed and permeabilized, for example, by treatment with a protease such as proteinase K, pronase, trypsin, pepsin, or the like. The telomerase-extended substrate is then amplified in situ by any of various methods known in the art, for example, using a primer extension reaction (e.g., employing established PCR or LCR protocols or primed-in situ labelling (PRINS; Koch, J., in "Nonradioactive in situ Hybridization Application Manual" (1992), Boehringer Mannheim, 31–33) or by other methods as described below. The presence of a signal in a cell during microscopic examination corresponds to the presence of telomerase activity.

Important Features of the Telomerase Substrate

Regardless of the origin of the sample, the sample (or an aliquot thereof) is assayed in a reaction mixture comprising a telomerase substrate. The particular telomerase substrate chosen in each case may vary depending on the type or origin of the telomerase activity for which one is testing, or the type of amplification or detection method employed. The telomerase activity expressed by one organism may differ with respect to substrate specificity from that expressed by another organism. Consequently, if one is using the present method to determine whether a cancer cell of human origin is present in the sample, one employs a telomerase substrate recognized by human telomerase.

A variety of substrates are known for the telomerases of Tetrahymena, other fungi, mammalian, and human cells and can readily be identified for other types of cells. However, when one employs a DNA polymerase-based primer extension step, the present method requires that the telomerase substrate not comprise a complete telomeric repeat sequence to minimize primer-dimer formation. Those of skill in the art will recognize that the telomeric repeat sequence produced by telomerase activity will depend upon the origin of the telomerase. For instance, Tetrahymena telomerase adds repeats of sequence 5'-TTGGGG-3' to the ends of telomerase substrates, while human telomerase adds repeats of sequence 5'-TTAGGG-3'. Thus, if one is using the present method to assay for human telomerase activity, the telomerase substrate should be a human telomerase substrate lacking the complete repeat sequence 5'-TTAGGG-3'. There is no requirement that a human telomerase substrate lack a telomeric repeat sequence from an organism that has a telomerase that adds a different repeat, so long as the presence of that different repeat sequence does not produce undesired results, such as excessive primer-dimer formation, as discussed further below.

In addition to linear single stranded or duplex nucleic acids, the substrate can be a circular plasmid DNA that undergoes linearization at a specific site, either inducibly or spontaneously. Such a plasmid substrate is particularly useful for in situ applications. An illustrative plasmid telomerase substrate is a vector that contains an insert with a unique restriction site (e.g., Isce I) located 3' to the telomerase substrate sequence. In this context, "unique" means that the restriction site is not present in the genome of the cell under analysis. Preferably, the vector is a selectable, multi-copy vector with a mammalian origin of replication. The method can further include a second expression plasmid that contains a gene coding for a restriction enzyme specific for the unique site, under the control of an inducible promoter. The two plasmids are co-infected into the target cell by methods known in the art, and are replicated. Upon induction of the expression plasmid product, the restriction enzyme cleaves the DNA of the telomerase substrate plasmid at the unique restriction site resulting in a linearized substrate plasmid, the ends of which are recognized as a telomerase substrate and can be elongated with TTAGGG repeats by telomerase.

There is a requirement for the telomerase substrate to lack telomeric repeat sequences in some instances, in particular where the replication step of the present method involves the hybridization of a primer or probe to extended telomerase substrates. For example, in some embodiments, the non-telomerase-mediated primer extension reaction involves hybridization of an oligonucleotide primer that hybridizes only to extended telomerase substrates. This addition is made under conditions such that, if extended telomerase substrates are present, the primer binds to the extended substrates and is then extended by enzymatic action.

Because telomerase can extend the telomerase substrate only by the addition of telomeric repeats, the primer will necessarily comprise a sequence complementary to a telomeric repeat. If the telomerase substrate employed in the telomerase extension reaction comprised a complete telomeric repeat, then the primer employed in the primer extension reaction could hybridize readily to unextended telomerase substrate, with potentially negative consequences. The telomerase substrate can, however, comprise sequences highly related to a telomeric repeat sequence without compromising the validity of the results obtained. For instance, an especially preferred human telomerase substrate of the invention is oligonucleotide M2, also known as TS, which contains a sequence at its 3'-end that is identical to five of the six bases of the human telomeric repeat but otherwise contains no complete telomeric repeat sequences. There is no requirement that the telomerase substrate be free of telomeric repeat sequences where the replication or detection method is not compromised by the presence of such repeats in the substrate, i.e., where primer extension is mediated by a ligase activity, or replication is achieved by means in which specific hybridization of a probe or primer to a telomeric repeat sequence is not problematic.

Replication of Telomerase-Extended Substrates to Enhance Detection (i) Primer Extension The primer extension reaction conducted subsequent to the telomerase substrate extension serves to amplify the signal produced by the presence of telomerase activity in a sample (extended telomerase substrates) by producing a second signal (extended primers). The primers can be extended by any means that requires the presence of extended telomerase substrates for primer extension to occur; preferred means are mediated by a template-dependent DNA or RNA polymerase, a template-dependent DNA ligase, or a combination of the two. With these means, if telomerase activity is present in the sample, an extended telomerase substrate is formed and then hybridizes to a primer, providing a substrate for either DNA or RNA polymerase or DNA ligase to produce a primer extension product.

Once a primer extension product has formed, one can disassociate (typically by heating, but one could also use an enzyme or chemical process, such as treatment with helicase) the extended primer from the extended substrate. If additional primer and primer extension reagent is present in the sample, then a new primer/extended telomerase substrate complex can form, leading to the production of another extended primer. One can repeat the process of primer extension and denaturation several to many times, depending upon the amount of signal desired. Typically, primer extension and denaturation of extended primer/extended telomerase substrate complexes will be performed at least 5, 10, 15, 20 to 30 or more times. Moreover, if a second primer complementary to the 3'-end of the extended primer is present in the reaction mixture, one can increase the signal (both extended primer and also additional extended telomerase substrate) dramatically. Unextended telomerase substrate still present in the reaction mixture during the primer extension step can function as such a second primer.

Those of skill in the art will recognize that if the primer extension reagent is a DNA polymerase, and a second primer is present, one has the requisite components for a polymerase chain reaction, more fully described in U.S. Pat. Nos. 4,683,195; 4,683,202; and 4,965,188, provided the appropriate buffer and nucleoside triphosphates are present in the reaction mixture. PCR amplification is a preferred mode for conducting the primer extension reaction step of the present invention and dramatically increases sensitivity, speed, and efficiency of detecting telomerase activity as compared to the conventional assay. The protocol is termed "TRAP" for Telomeric Repeat Amplification Protocol and is illustrated, inter alia, in Example 2. The telomerase substrate can also conveniently serve as a PCR primer (termed the "upstream primer"), although many other primer sequences can also be used. The sequence of the other primer is chosen to avoid annealing of the telomerase substrate and the primer, because even minor levels of primer/telomerase substrate annealing can yield early cycle PCR products identical to telomerase products (e.g., TS plus (5'-AG[GGTTAG]$_n$-3'), where n equals 1, 2, 5, 10, or more. In subsequent cycles, these products could serve as template for the production of PCR products, potentially resulting in a false positive result.

The present invention provides a variety of oligonucleotide primers and telomerase substrates for use in the PCR-based embodiment of the present invention. One such primer (termed the "downstream primer") is designated "CX" and is composed of sequences complementary to three imperfect telomeric repeats and one perfect repeat, 5'-(CCCTTA)$_3$CCCTAA-3' (SEQ ID NO:1). The single nucleotide difference in three of the repeats compromises the capacity of CX to anneal to the telomerase substrate TS (which, as noted above, contains 5 of 6 nucleotides of a telomeric repeat) by creating a 3' mismatch in the TS/CX duplex, thereby minimizing the formation of non-specific PCR products, such as primer-dimer. Any possible alignment between these primers (CX and TS) nucleated by the telomeric sequence complementarity leads to a duplex in which the recessed 3' nucleotide is mismatched and so is not efficiently extended by polymerase.

As the CX primer demonstrates, and as those of skill in the art will recognize upon review of this disclosure, a primer with sequences "complementary to a telomeric repeat" includes a primer that may contain one or more mismatched bases with respect to the telomerase substrate extension product to which the primer is intended to hybridize. The number of mismatches that can be tolerated within this definition can vary depending upon the length and sequence composition of the primer, the temperature and reaction conditions employed during the PCR step, the purpose for which the assay is conducted, and the results desired.

In addition to primer CX, the present invention provides several modifications of a basic PCR that, while not necessary to obtain the benefits of the present method, can greatly enhance the specificity, sensitivity, and efficiency of the present method for some applications and in certain embodiments. For instance, one important modification to the in vitro method relates to the buffer: the present invention provides a buffer in which both telomerase activity and DNA polymerase activity can be observed. The use of such a buffer allows the artisan to conduct both the telomerase substrate extension reaction and a DNA polymerase-mediated primer extension reaction in the same reaction vessel, for example, in a tube (see Example 2).

Another modification relates to the use of relatively short oligonucleotides that are complementary to either the telomerase substrate or the return primer in the reaction mixture. These short oligonucleotides are designed to have a melting temperature (with respect to the primer or telomerase substrate to which the short oligonucleotides hybridize) about 10° C. lower than the annealing temperature of the primers used in the primer extension step and to prevent primer-dimer formation and/or non-specific primer extension, particularly at low temperatures. The short oligonucleotides melt away from their complementary oligonucleotides at temperatures just below the ideal annealing temperatures for the primer extension step, preventing inappropriate primer extension at lower, non-specific temperatures. Given that the short oligonucleotides are not intended to serve as primers for DNA synthesis, the 3'-end of the short oligonucleotide can be blocked to prevent addition of nucleotides to the short oligonucleotide. If the short oligonucleotide is designed to hybridize to the primer, then the 3'-end of the short oligonucleotide should be blocked (e.g., with biotin, phosphate, digoxigenin, a fluorescein or an amino group) to prevent the short oligonucleotide from serving as a telomerase substrate.

A variety of other reagents and formats can be employed to ensure a high degree of specificity, including: (1) the use of T4 gene 32 protein (available, e.g., from Boehringer Mannheim); (2) the use of TaqStart™ antibody (available, e.g., from Clontech); and (3) the separation of the primer from the other reaction components by a wax barrier (e.g., Ampliwax™, available from Perkin Elmer) that melts only after the reaction mixture is heated at the end of the telomerase-mediated extension reaction. The purpose of the wax barrier is to separate the telomerase extension reaction from the amplification reaction. Thus, as one example, and there are many examples, the DNA polymerase can be sealed under a wax layer thus separating it from other reaction components. Alternatively, the primer can be sealed under a wax layer or barrier at the bottom of a tube with the other reaction components positioned on top of the barrier.

For ease of preparation, reaction components can be attached to solid matrices, such as polystyrene beads of about 1 micron to about 5 millimeters in diameter; plates or the wells of a microtiter plate such as those made from polystyrene or polyvinylchloride; glass beads; magnetic particles; polysaccharides; or other surfaces that can be coated, e.g., with primer. The primer is typically affixed to the solid matrix by adsorption from an aqueous medium although other modes of affixation, as is well known to those of ordinary skill in the art, can also be used. For example, the solid surface is contacted with a solution of the primer and dried until the surface is coated with an appropriate amount of primer. The amount of primer coated on the solid surface can be varied by adjusting the concentration of primer in the contacting solution. The primer-coated solid matrix is then covered with hot molten wax that is left to solidify. The wax barrier thus isolates the primer from the other reaction components (e.g., the telomerase substrate, dNTPs, buffer, DNA polymerase or ligase) until a temperature is reached at which the wax melts. These formats ensure that the return primer will be accessible to the other reagents only at temperatures that ensure highly specific nucleic acid basepairing and so reduces non-specific primer extension and primer-dimer (composed of a primer and an unextended telomerase substrate) formation. In addition, tis format allows one to conduct the activity assay in a single reaction tube and provides a convenient format for packaging the reaction components. Thus, one useful kit of the invention comprises a reaction tube or other solid support having a primer or polymerase separated from the telomerase reaction buffer and/or other reagents by a wax barrier.

The primer extension methods of the present invention have been used to test for telomerase activity in human cell lines and normal somatic cells as illustrated in Examples 2. Telomerase-positive extracts from human 293 kidney cells were produced routinely from $10^5$ cells, as assessed by TRAP assay, with a lower limit for the conditions employed in this particular example of $10^2$ cell equivalents for detection of telomerase activity. These results demonstrate at least 100-fold improvements in both extraction efficiency and telomerase activity detection when compared to conventional methods and together increase current detectability of telomerase activity by a factor of at least $10^4$. The telomerase activity assay method of Example 2 has been used to test for telomerase activity in various immortal cell lines and normal somatic cell cultures from different tissues and individuals, as illustrated by Example 3 below. As shown in Example 3, the difference in telomerase activity between immortal and normal somatic cells was estimated to be at least 1000-fold, supporting a direct role for telomerase in telomere dynamics in human cells.

Those of skill in the art will recognize the detection limits noted above are valid only if one employs merely routine procedures. The present method can be used to detect telomerase activity in a single cell, provided one is willing to use effort somewhat greater than what is typically considered routine, primarily for the single cell isolation step. One can increase the time of the telomerase-mediated extension step, increase the purity of the test extract for telomerase, increase the amount of labels used in the assay, and increase the number of primer extension cycles to increase the sensitivity of the assay to detect telomerase activity in a few cells or a single cell. Example 11 illustrates this aspect of the invention.

The PCR-based embodiment of the present invention offers significant improvements over currently available methods for measuring telomerase activity in a sample. Other novel variations of the present method, however, also offer significant advantages. In particular, the present method can be used to quantitate the telomerase activity in a sample by providing the number of telomerase products generated. To understand the nature of these improvements, however, one should first consider more carefully the ladder of bands produced upon gel electrophoresis of telomerase extended substrates. Such results reflect the number of repeats added by telomerase during the telomerase-mediated extension reaction, but in certain PCR-based embodiments of the present inventions, some of these products can result from staggered binding of primers during the PCR amplification steps.

The phrase "staggered binding" refers to the binding of a primer to a sequence in an extended telomerase substrate in a manner that leaves the 3'-end of the extended telomerase substrate recessed and therefore available for extension by DNA polymerase. In such a configuration, DNA polymerase can add nucleotides to the 3'-end of the extended telomerase substrate, creating molecules longer than those produced in the telomerase-mediated extension step. To determine whether staggered binding was occurring in reactions such as those described in Example 2, synthetic oligonucleotides representing discrete telomerase extension products, e.g., TS+4 (TS plus four telomeric repeats), were used to develop specific amplification conditions. Even under high stringency, staggered annealing of the downstream primer occurred (e.g., annealing by 3 of the 4 repeats). Hence PCR amplification of a discrete telomerase extension product yielded a six nucleotide ladder of PCR products increasing in size up to the limit of gel resolution. Thus, TRAP assay products produced using a primer such as CX are not directly reflective of the length distribution of telomerase products generated in the telomerase substrate extension step, due to the staggered binding of primers to templates during the primer extension reactions.

In some cases, however, for example in in situ telomerase assays, it can be advantageous to have staggered binding resulting in larger molecules that prevent leakage of the telomerase products out of the cell. However, in in vitro assays, it may sometimes be preferable that such interactions be prevented by employing a novel "anchored" primer of the invention as the downstream primer in the assay. For purposes of the present invention, an anchor sequence is a 5'-terminal sequence of a PCR primer that is a non-telomeric repeat sequence (a sequence neither complementary nor identical to a complete telomeric repeat sequence) and that prevents the PCR product from "growing" on itself, for example as observed when the primer pairs TS/(CTR)$_4$ or TS/CX are employed. Thus, such an oligonucleotide can comprise a 6 nucleotide anchor sequence (although the length is not critical and can be 3 to 5 to 15 to 30 or more nucleotides) at its 5'-end followed by three repeats of CTR (C-rich telomeric repeat; 5'-CTAACC-3') sequence (e.g., the ACT primer; 5'-GCGCGG[CTAACC]$_3$-3'; SEQ ID NO:2 is an anchored primer of the invention).

A wide variety of anchor sequences can be employed. In one embodiment, the anchor sequence is the sequence of the telomerase substrate used in the telomerase-mediated extension step of the method, providing a "TS-anchored" primer (note that, in this context "TS" represents any telomerase substrate lacking a complete telomeric repeat sequence). The anchored primer would thus comprise, in the 5'-to-3' direction, a telomerase substrate sequence and two or more complementary copies of the telomeric repeat sequence. By employing such a primer, one can practice the present method in what is essentially a "one primer" mode, because after the first round of primer extension, excess unextended telomerase substrate in the reaction mixture can prime the synthesis of both strands of the duplex formed as a result of the first round of primer extension.

By using, for example, the primers TS (5'-AATCCGTCGAGCAGAGTT-3'; SEQ ID NO:3) and ACT (or another anchored primer) in the TRAP assay, one can deduce the Most Processive Product (MPP) of the telomerase in a given extract. The use of an anchored primer such as ACT prevents the growth of telomerase products into longer versions during PCR. With the ACT primer, the slowest migrating band reflects directly the length of the MPP of the original telomerase products before the PCR. Without such primers, multiple cycles of primer extension and product denaturation can yield primer extension products that comprise many more telomeric repeats than present in the telomerase-extended telomerase substrates originally present in the reaction mixture after the telomerase substrate extension reaction. The ACT primer is particularly preferred for purposes of the present invention in that it is more resistant to the types of primer-dimer interactions observed between TS and primers such as CX or CTR$_4$. Alternatively, a hybrid oligonucleotide can be used as a return primer. The hybrid has an anchor sequence followed by a primer-based sequence that contains mismatches in the complementary telomeric repeats, for example, ACX 5'-GCGCGG [CTTACC]$_3$CTAACC-3' (SEQ ID NO:4) that has mismatches in 3 of 4 complementary telomeric repeats. This results in a primer that has the ability to destabilize primer-dimer formation (like a CX primer) and to predict the most processive telomerase product from the TRAP assay (like an ACT primer). Furthermore, the resulting ACX is more resistant to primer-dimer formation than either the ACT or CX primer. The utilization of the ACX primer in the TRAP assay provides similar benefits as the wax-barrier methodology in preventing primer-dimer formation, but simplifies the analysis, manufacture, and performance of the TRAP assay.

The TRAP assay can be further improved by reducing non-specific, template-independent, PCR artifacts (e.g., primer-dimer) by means other than or in addition to oligonucleotide selection and the use of a hot-start wax barrier. For example, the addition of dimethyl sulfoxide (DMSO), optionally with glycerol, to the TRAP assay buffer destabilizes the interactions between the telomerase substrate primer (e.g., TS) and the return primer (e.g., CX, ACT) thereby increasing the reliability of the TRAP assay. Similarly, the use of a DNA polymerase or fragment thereof (e.g., the Stoffel fragment of AmpliTaq™ DNA polymerase; Perkin Elmer) that lacks a 5' to 3' exonuclease activity can be employed to prevent primer-dimer artifacts. When a primer, such as CX or a CX-based primer, hybridizes to a template (e.g., TS), the 3' mismatch of the primer should prevent primer extension. However, DNA polymerases with inherent 5' to 3' exonuclease activity are able to remove the 3' mismatched nucleotide and extend the primer. In contrast, a DNA polymerase or fragment that lacks a 5' to 3' exonuclease activity is unable to cleave the mismatched nucleotide and thus helps prevent misextension of primers and primer-dimer artifacts.

The present invention also provides a variety of means to quantitate the amount of telomerase in a sample, although for most purposes, a qualitative result (telomerase activity present or absent) is sufficient. One important means for obtaining quantitative information is the use of a control oligonucleotide template added to each reaction mixture in a known amount, as illustrated below in Example 4.

An illustrative competitive control oligonucleotide of the invention comprises, in 5'-to-3' order, a telomerase substrate sequence, a spacer sequence (preferably 3 nucleotides in length, but which can be any sequence of nucleotides or length; a length of 3 nucleotides ensures that the internal control is different from that from the extended substrates, and a telomeric repeat sequence (typically present in multiple, e.g., 2 to 50, copies). Of course, an oligonucleotide complementary to the control sequence defined above can also serve as the control sequence, or a double-stranded control nucleic acid, or plasmid with a double-stranded nucleic acid insert can be employed. Use of this internal control not only facilitates the determination of whether the assay was conducted properly but also facilitates quantitation of the telomerase activity present in the sample.

Alternatively, one can add a control nucleic acid of any sequence to the reaction mixture in known amounts and amplify the control with primers different from those used to amplify the extended telomerase substrate (non-competitive internal control). The control oligonucleotide and/or the primers used to amplify the control oligonucleotide can be labelled identically to or differently from the label used to label the telomerase extension products. A preferred internal control oligonucleotide comprises a combination of the controls described above where, in the PCR embodiment of the invention, the internal control competes with the telomerase extension product for only one primer and is thus termed a semi-competitive control. Such a control comprises, in 5'-to-3' order, a sequence that is not a substrate for telomerase or a telomeric repeat, or a complementary sequence thereof followed by a telomeric repeat sequence. One can also design internal controls that can be amplified by a single primer, as is evident to those of ordinary skill in the art. An alternative semi-competitive control comprises, in 5'-to-3' order, a telomerase substrate sequence followed by a sequence that is neither a substrate for telomerase nor a telomeric repeat or a complementary sequence thereof. The control can also be designed to be separated easily from the TRAP products for quantitation. An example of such a semi-competitive internal control is 5'-AATCCGTCGAGCAGAGTTAAAAGGCCGAGAAG-CGAT-3' (SEQ ID NO:5; TSNT) that can be amplified by the TS telomerase substrate primer and the NT primer 5'-ATCGCTTCTCGGCCTTTT-3' (SEQ ID NO:6). The NT primer is not a substrate for telomerase. The TSNT oligonucleotide is employed in a TRAP assay with TS, ACX (or any other return primer) and NT, and the resulting 36 bp control duplex DNA is easily distinguished from the telomerase extension products, the smallest of which is 50 bp. The control oligonucleotide can also be conveniently packaged into a kit with other reaction components.

To detect the presence of a nucleic acid in a sample, the TaqMan™ (Perkin Elmer) detection system can be employed. This system is suitable for use in the telomerase assays of the invention and provides a rapid detection method that is non-radioactive and readily modified to a multiwell system. A target specific probe that possesses both a fluorescent reporter dye tag and a quencher dye tag is incorporated into the primer extension reaction (e.g., PCR amplification). Although there is no precise limitations on the positions of these tags, it will be apparent to one of ordinary skill in the art that particular positions may be preferable to others; for example, the tags are preferably positioned 6–8 nucleotides apart. The TaqMan™ probe hybridizes to the target sequence at an internal site under primer extension conditions and, if the primer is extended by the action of a DNA polymerase having 5'-3' exonuclease activity, the 5'-3' exonuclease activity of the polymerase degrades the hybridized probe freeing the reporter dye/dNTP from the proximity of the quencher dye. The increase in the free reporter dye/dNTP complex results in an increase in fluorescence that is proportional to the amount of amplified product (Livak et al., January 1995, Research News, Perkin Elmer Corporation, 1-5; Lee et al., 1993, *Nucl. Acids Res.* 21:3711≧3766). In a typical TaqMan™ PCR application, where the target is generally a double stranded DNA of 100 bp-1 kb in length, selection of three specific hybridization sites (one site for the forward primer, one site for the return primer and one site for the TaqMan™ probe) is easily accomplished. However, in the TRAP assay, the choice of specific hybridization sites available for the TaqMan™ probe and the two primers is limited. These sites comprise the telomerase substrate sequence (e.g., TS; 5'-AATCCGTCGAGCAGAGTT-3'; SEQ ID NO:3), and the telomeric repeat sequences (e.g., TTAGGG), or their complementary sequences, with or without mismatches. For example, a TaqMan™ probe that comprises C-rich telomeric repeat (CTR; 5'-CCCTAA-3') sequences can be used (e.g., a probe that comprises four repeats of CTR; this probe is termed CTR$_4$). Although TaqMan™ probes are generally blocked at their 3' ends, and thus cannot be elongated during PCR amplification, the CTR probes could compete with the ACT primer (or other return primers) as they hybridize to the same sites, which can lead to a reduction in PCR efficiency. Furthermore, because the probe can anneal to the telomerase substrate, such as TS, the use of hot-start PCR methodology in the assay may be useful; this can readily be accomplished by separating the probe and the return primer with a wax barrier from the remaining reaction components.

A preferred TaqMan™ probe consists of a sequence complementary to the telomerase substrate; therefore such a probe does not compete with either the forward or return primers, and thus does not result in primer-dimer formation. Such a probe can form a duplex with the forward primer (e.g., TS), which can decrease PCR efficiency during exponential amplification. However, telomerase can recognize and extend double-stranded substrates (see Example 8), and the reaction can proceed in the presence of forward primer-probe duplexes.

Alternatively, a TaqMan™ probe that consists of a sequence complementary to the 3' region of the forward primer, followed by a telomeric repeat sequence (e.g., CTR sequence), can be used. Such a probe specifically hybridizes to the junction between the forward primer and the telomeric repeat sequence and reduces not only competitive effect with the return primer but also forward primer-probe duplex formation. With such a probe, generation of primer-dimer artifacts can be avoided by using hot-start TRAP methodology. For example, a probe comprising the sequence 5'-AACCCTAACCCTAACTCTGCT-3' (SEQ ID NO:7), corresponding to the junction sequence between the 3' end of TS and the telomeric repeats of the telomerase product, can be used. Alternatively, mismatches can be introduced into such probes to minimize potential interference with the telomerase substrate extension reaction, i.e., by minimizing probe binding to TS during the extension step. For example, probes having the sequence 5'-CCTAACCCTAACCCCACTATGCT-3' (SEQ ID NO:8) or 5'-CCTAACCCTAACCCTGTATATGCT-3' (SEQ ID NO:9) can be used in this embodiment. Conditions are selected to allow the probe to bind preferentially to the extended telomerase substrate during the PCR reaction.

A TaqMan™ probe consisting of the telomerase substrate sequence or telomere repeat sequences (e.g., 5'-TTAGGG-3') can also be used in the TaqMan™ detection system. However, in addition to the potential formation of primer-dimers and primer competition discussed above, these probes may compete with the telomerase substrate for telomerase, although competition can be minimized using hot start methodology.

In another embodiment of TaqMan mediated extension, reporter and quencher dyes are present at the two ends of a return primer with a 3' mismatch, as exemplified by the primer MACX, which has the sequence 5'-GCGCGG[CTTACC]$_3$CTAACCAAT-3' (SEQ ID NO:10), without 3' blocking of the primer. When such a primer is used in the TRAP assay with a thermostable DNA polymerase with proof-reading capability, the mismatched nucleotide at the 3' end of the primer is cleaved by the exonuclease activity releasing the reporter dye from the quencher prior to extension. Thus, any amplification using such a primer results in a fluorescent signal. This embodiment of the invention is not limited to fluorescence quenching, as other proximity indicating signals can be used; for example, a probe can be labelled with a radioactive label and detected with a scintillant.

Those of skill in the art recognize that the method of the invention can involve the correlation of telomerase activity in a sample with the formation (presence in the reaction mixture) of duplex nucleic acids composed of extended telomerase substrates annealed to extended primers. One can infer the presence of such molecules by the presence of either (1) an extended telomerase substrate; (2) an extended return primer; (3) a duplex nucleic acid comprising both (1) and (2); or (4) hybridization of a probe to any of the foregoing. In any event, however, one will typically make this correlation by detecting the presence of extended telomerase substrates and/or primers via a label incorporated into or attached to one or more of the reaction products, although the Taqman™ detection method described above is perhaps an exception to this rule.

While the PCR-based embodiment of the present method has been described in detail above and is exemplified in the Examples below, the present method can be practiced using any method of primer extension to provide target amplification or with a method that provides for signal amplification or both, as described below. In addition, while PCR provides for exponential accumulation of primer extension products, even linear accumulation of primer extension products can provide useful results. Thus, one can use a single primer and merely make many copies of the telomerase-extended substrate.

Moreover, such copies can be made by means other than polymerase-mediated primer extension, as described more fully below. One such method is the ligase chain reaction (Barany, 1991, *Proc. Natl. Acad. Sci. USA* 88:189–193). Copies of the telomerase extension products can be made using DNA ligase to ligate together two oligonucleotides hybridized to the extended telomerase substrate. If, as in PCR, the duplex nucleic acid is then denatured, then one can repeat the process of ligation and denaturation many times to accumulate many complementary copies of the original extended telomerase substrate. If one additionally adds two other oligonucleotides complementary to the copy produced by ligation of the first two oligonucleotides on the extended telomerase substrate and selects those oligonucleotides such that DNA ligase can ligate the two together to form an identical (as opposed to complementary) copy of the original extended telomerase substrate, then one has the basic components of an LCR. To illustrate, one could employ LCR in the present method using the following four oligonucleotide "ligomers":

LTS (5'-CCCAATCCGTCGAGCAGAGTTAG-3')(SEQ ID NO:11),
CLT (5'-TAACTCTGCTCGACGGATTCCC-3') (SEQ ID NO:12),
LC (5'-GGGTAACCCTAACCCTAACCC-3') (SEQ ID NO:13), and
LG (5'-GGTTAGGGTTAGGGTTAAA-3') (SEQ ID NO:14).

The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. A wide variety of such ligomers can be used in the method to minimize template-independent product formation. LCR amplification of telomerase extension products produces an amplified product of uniform size and so is conducive to quantitative analysis. Furthermore, a combination of a thermostable polymerase and a ligase with primers, such as, for example TS, LC, and CLT, can be used to amplify telomerase-extended substrates.

(ii) Oligonucleotide Proximity Assay

In a further aspect of the invention somewhat related to the LCR method described above, oligonucleotides complementary to adjacent portions of the telomerase extension product (e.g., LC and CLT) are employed to detect the presence of telomerase extension product. The oligonucleotides are constructed so that when annealed to the telomerase extension product, the 5'-end of one oligonucleotide can be ligated to the 3'-end of the other. One of the oligonucleotides is labelled with a fluorescent "reporter" label and the other with a "quencher" label. For example, the components can both be fluorescence emitters with the absorbance spectrum of the first being selected to overlap with the emission spectrum of the second; an example of such a pair would be fluorescein and rhodamine. Upon annealing of the oligonucleotides to the telomerase product, the quenching effect resulting from the proximity of the reporter to the quencher can be detected as an indication of telomerase extension products. Subsequent ligation of the annealed oligonucleotides is required for further amplification by LCR, although ligation is not required for detection using the assay.

This detection system is not limited to fluorescence and quenching but can be used with probes comprising any two components that interact in a detectable manner through adsorption, modulation, or emission of electromagnetic or nuclear radiation. Detection can, for example, be mediated by chemical, enzymatic or radiation events. For example, a radioactive label and a scintillant, or an enzyme pair in which the product of one enzyme is a substrate for the second can be used to provide a proximity signal. Any proximity indicating pair resulting in a detectable signal can be used; detection can be fluorometric, radiometric, or colorimetric, for example.

(iii) RNA Polymerase-Mediated Replication

In one aspect of the invention, telomerase extended products are replicated by means of the action of an RNA polymerase. A variety of methods for replicating nucleic acids using an RNA polymerase are known, e.g., nucleic acid sequence-based amplification (Compton, 1991, *Nature* 350:91–92), self-sustained sequence replication (Guatelli et al., 1990, *Proc. Natl. Acad. Sci. USA* 87:1874–1878), and strand displacement amplification (Walker et al., 1992, *Proc. Natl. Acad. Sci. USA* 89:392–396). In a preferred embodiment, an RNA polymerase that utilizes a single stranded DNA template (e.g., N4 RNA polymerase) is employed to synthesize an RNA copy from a single-stranded DNA template using a promoter sequence at the 5' end of the template. The telomerase substrate can comprise a promoter sequence operably linked to its 5' end or the promoter can be ligated to the substrate after extension of the substrate and prior to replication with the RNA polymerase. Many RNA transcripts can be generated from a single DNA template thereby increasing the number of the target molecules. One can optionally employ a reverse transcriptase to make DNA copies of the RNA transcript.

Alternatively, the method employs a non-telomeric telomerase substrate sequence (e.g., TS) that can be extended by telomerase and, a return primer, e.g., $CTR_3$ (comprising 3 repeats of the CTR sequence) that is complementary to telomeric sequences. A DNA polymerase (e.g., Taq polymerase, Klenow fragment, Stoffel fragment of Ampli-Taq™ polymerase) is then used to synthesize a cDNA complementary to the telomerase extension product. An RNA polymerase that recognises a double stranded substrate (e.g., T7 polymerase, T3 polymerase, SP6 polymerase) is then used to synthesize multiple RNA copies of the duplex telomerase extension product as directed by a promoter sequence incorporated into the 5'-end of the telomerase substrate or return primer. Any of a variety of promoters, e.g., T7, T3, SP6 promoters, can be used for this purpose. The promoter sequence can be present during the telomerase extension step or ligated at a later stage to the extension products.

As noted above, amplification can also be achieved by using nucleic acid sequence-based amplification (NASBA). In this embodiment, an RNA polymerase (such as T7 RNA polymerase) synthesizes RNA copies of the extended telomerase substrate essentially as described above. A reverse transcriptase is used to synthesize DNA copies of the RNA, RNaseH degrades the RNA strand and the single stranded DNA acts as a template for RNA synthesis, thus providing cyclic amplification. Alternatively, reverse transcriptase can be used to synthesize cDNAs, or RNA polymerase can be used to extend primers, and the products can be amplified by primer extension (e.g., with PCR). These and other variations of the present method will be apparent to those of skill in the art upon consideration of this disclosure. In these embodiments, the presence and level of telomerase activity is correlated to the presence of RNA copies of the extended telomerase substrate. As in other embodiments, a wide variety of primers can be designed (for example, to decrease background), as would be apparent to one of ordinary skill in the art.

(iv) Branched DNA-Mediated Replication

In another embodiment, telomerase extension products are either first replicated and/or then detected using branched DNA (bDNA) signal amplification (Urdea, 12 Sep. 1994, *Bio/Tech.* 12:926–928; U.S. Pat. No: 5,124,246) which involves amplification of the signal produced upon probe hybridization to a target nucleic acid. The assay for detecting telomerase activity with bDNA can be carried out in a multi-well plate, a format that is particularly useful for screening, because the assay is simple to perform with multiple samples, and commercial hardware is available. Furthermore, conditions can be chosen to allow quantitative detection of telomerase activity. Any telomerase substrate (e.g., TS oligonucleotide 5'-AATCCGTCGAGCAGAGTT-3'; SEQ ID NO:3) can be used, and the substrate is incubated with a cell extract, allowing any telomerase present to extend the substrate (optionally bound to a solid support to facilitate detection) with the addition of telomeric repeats. In one embodiment, the substrate is linked at its 5' end to a well of a multi-well plate (or other solid surface) using conventional chemical techniques. Multi-well plates with linked oligonucleotides are also available commercially (Chiron Corp.). Alternatively, the telomerase substrate is bound by hybridization to a complementary oligonucleotide bound to the solid surface. The telomerase extension reaction can occur on bound oligonucleotide substrate or on free oligonucleotide substrate that is bound at a later stage.

The bDNA probe is comprised of a hybridizing portion complementary to the telomeric repeats (e.g., 5'-(CCCTAA)$_n$-3' or its permutations) and so hybridizes with extended telomerase substrates. The probe further comprises a branched region that provides multiple secondary probe binding sites. After washing to remove unbound probe, a labelled secondary probe specific for the branches of the bDNA is hybridized to the bDNA and is detected via the label.

The artisan recognizes that this format is amenable to many variations; for example, the telomerase substrate can be immobilized after extension by telomerase by capturing the telomerase extension products by hybridization to immobilized oligonucleotides complementary to telomeric repeats and detecting the products by hybridization to a probe complementary to the telomerase substrate. The signal increases in direct proportion to the secondary probe-accessible-sites on the bDNA molecule, thus a rare population of target nucleic acids can be detected by bDNA hybridization. Sensitivity can be further enhanced by probing the telomeric-repeat-complementary-bDNA (or telomerase substrate-complementary-bDNA) with a secondary bDNA probe specific for the branches of the primary bDNA probe (and a tertiary probe specific for the secondary probe, etc.), thereby presenting more numerous hybridization sites for the labelled probe.

The use of bDNA to probe for extended telomerase substrates is not limited to use with cell extracts but can also be applied to the in situ methodology of the present invention. Extended telomerase substrates in cells fixed onto a microscope slide, for example, can be probed with bDNA instead of conventional linear nucleic acid probes. However, to facilitate the internalization of the bulky bDNA probes, shorter branch lengths are preferred. Thus, for in situ detection using bDNA, the branches are usually less than about 60 nucleotides in length, preferably less than about 40 nucleotides in length. The improved probe uptake overcomes any decrease in sensitivity of the assay that may occur resulting from shorter branch length. Furthermore, the combination of a secondary bDNA probe specific for the branches of the primary bDNA probe, both bDNA probes having short branches, provides additional sensitivity. The bDNA methodology can also be applied to the detection of primer extension products, as would be understood by one of ordinary skill in the art upon reading this disclosure.

Signal amplification can be achieved by using a probe other than bDNA which hybridizes to a target nucleic acid, and probe detection, including bDNA probe detection, can be used in many of the embodiments of the invention. For example, a telomerase substrate can be immobilized to a solid surface, e.g., a well of a microtiter plate, a tube, or beads. The telomerase assay is employed to extend the telomerase substrate with telomeric repeats (e.g., TTAGGG). The reaction can be stopped, if desired, by washing the solid surface to remove soluble reactants, by the addition of denaturing amounts of detergent or divalent cation chelators, by heating, or by other means. Extended telomerase substrate is then probed with a labelled nucleic acid complementary to the telomeric repeats. Typically the nucleic acid probe (DNA, RNA, or peptide nucleic acid (PNA) or other nucleic acid analogues) is directly labelled, although hybridization to a further labelled probe is possible, as is recognized by the artisan. A particularly preferred probe is a polybiotinylated nucleic acid that can be detected by tyramide signal amplification, as described in U.S. Pat. No. 5,196,306. Horseradish peroxidase (HRP)-linked streptavidin binds to the biotin, and the HRP catalyzes the deposition of activated tyramide molecules labelled with fluorophores, biotin, or HRP, for further amplification, and thus the covalent deposition of fluorophores, biotin or HRP to the solid surface. The deposited labels can be detected by standard techniques.

Reagents

While the disclosure above and Examples below illustrate the invention with results obtained using oligodeoxyribonucleotide telomerase substrates, probes, controls, and primers or ligomers, the present invention is not so limited. Thus, one can employ oligoribonucleotides or oligonucleotides that comprise one or more modified (i.e., synthetic or non-naturally occurring) nucleotides as probes or primers. Usually, nucleotide monomers in a nucleic acid are linked by phosphodiester bonds or analogues thereof. Analogues of phosphodiester linkages include phosphorothioate, phosphorodithioate, phosphoroselenoate, phosphorodiselenoate, phosphoroanilothioate, phosphoranilidate, phosphoramidate, peptide, and the like linkages.

For example, PNA is an oligonucleotide with peptide bonds instead of phosphodiester bonds in its backbone. Because a PNA has no charge, a PNA has a higher binding affinity than a deoxyribonucleic acid. As another example, a phosphorothioate oligonucleotide having a telomeric or non-telomeric sequence can be prepared by methods known in the art and used as a telomerase substrate during the telomerase reaction. Unlike DNA polymerase, telomerase can recognize and extend phosphorothioate oligonucleotide substrates. The products of the telomerase reaction can then be detected by the methods described herein, except that amplification of an extended telomerase product using phosphodiester primers and a polymerase is asymmetrical unless another primer is added. Polymerases cannot utilize phosphothioate oligonucleotides as primers, so primer-dimer artifact formation is decreased in such an assay, although, compared to exponential amplification of the telomerase products, sensitivity of the assay may be compromised unless another primer is added. Sensitivity can be improved in this embodiment by using PCR-independent methods of replication or detection, such as by the use of branched DNA probes, as described above.

Those of skill in the art will recognize that the reagents employed are commercially available or, in the case of the oligonucleotides, can be prepared using commercially available instrumentation, and that a wide variety of DNA polymerases, antibodies, and single-strand DNA binding proteins can also be employed.

Detection of Replicated Telomerase-Extended Substrates

Regardless of the nature of the replication reaction, and as also noted above, the various reagents of the invention can be labelled to facilitate identification of telomerase-extended telomerase substrates or nucleic acids replicated therefrom in a reaction mixture. For instance, one can use one or more labelled nucleoside triphosphates, a labelled primer, or a labelled telomerase substrate (or a combination of the same) and monitor incorporation of the label into telomerase substrate or primer extension products. The internal control, if any, can also be labelled with the same or a different label. Any of a wide variety of labels can be used for purposes of the present invention. Such labels include fluorescent (e.g., fluorescein-5-isothiocyanate (FITC) and rhodamine), phosphorescent, chemiluminescent, enzymatic, and radioactive labels, as well ws various chromophores. A preferred fluorescent label is an intercalating dye. A particularly preferred fluorescent dye is SYBR Green I that exhibits enhanced fluorescence when bound to double-stranded nucleic acids but only minimal fluorescence with single-stranded DNA or RNA. Alternatively, the label can merely be an unlabelled "tag", which in turn is recognized by a labelled molecule that binds to the tag. For instance, one can use biotin as the tag, use avidinylated or streptavidinylated horseradish peroxidase ("HRP") to bind to the tag, and then use a chromogenic substrate (e.g., tetramethylbenzamie, TMB) to detect the presence of the HRP. In similar fashion, the tag can be an epitope or antigen (e.g., digoxigenin), and an enzymatically, a fluorescently, or a radioactively labelled antibody can be used to bind to the tag. A further example utilizes telomeric repeat binding proteins that are known in the art. Such proteins have been identified as binding either to double-stranded or single-stranded telomeric repeats and native or recombinant proteins can be used. Typically, such proteins would be purified for use and detected by virtue of a label attached to, or an antibody specific for, the particular protein.

Detection of the label may involve additional steps, depending on the needs of the practitioner and the particular label or detection means employed. In some instances, the practitioner may first separate reaction products from one another using gel electrophoresis, as exemplified below. Other separation methods, i.e., chromatography, can also be employed, but for some purposes, no separation will be performed, and the detection of extended telomerase substrates and/or primers will be carried out without removing the reaction mixture from the vessel in which the reaction was performed, as in a homogeneous PCR where one measures intercalation of a fluorophore in duplex DNA during amplification. One important advantage of the present invention is the adaptability of the method to any detection format of interest.

The Multiplex Electrophoretic Separator (MES) is useful in analysis of primer extension products or any other samples with a mixture of target nucleic acid and nonspecific dNTPs and/or primers (See Example 11) and is particularly useful for high throughput diagnostic assays. As shown in FIGS. 1A and 1B, the apparatus comprises a housing (1) containing a receptacle (2) adapted to receive a multiwell plate (3), and two electrodes (4). The electrodes are typically parallel to each other and preferably movably attached to the housing to allow insertion of a multiwell plate onto the receptacle (2) that retains the multiwell plate between the two electrodes, and have the same configuration as the surfaces of the multiwell plate (i.e., the electrode covers the surface of all wells present in the microtiter plate in preferred embodiments). The multiwell plate typically has 24, 48, 96 or more wells per plate, in single (i.e., a strip of microtiter wells) or multiple rows. Each well (5) is open at its upper surface (6) and has an open but sealable lower surface (7), e.g., a Silent Monitor™ 96 well plate, Pall Corp., with removable filter bottom, that can be resealed with adhesive tape. The microtiter plate is placed between two electrodes and connected to a means for applying an electrical current, such as outlets for connection to a power supply. The electrodes can be made of sheets of any electroconducting material, such as metallic sheets or wire metal grids (FIG. 1).

This apparatus can be used to separate a mixture of compounds in multiple samples by preparing an electrophoretic matrix, such as a polyacrylamide or agarose gel, in a sealed well. The seal is removed, the plate is placed in the receptacle (2) above an electrode, and the electrophoretic matrix is immersed in electrophoretic buffer. Alternatively, the buffer contacting the negative and positive electrodes can be provided in two chambers, where the only points of contact between the two chambers is through the electrophoretic matrix. The mixture to be separated is prepared for electrophoresis essentially as for conventional electrophoresis and then applied to the surface of the electrophoretic matrix. A second electrode is placed above the multiwell plate, and both electrodes are connected to a power supply, thus allowing separation of the components of the reaction mixture. Electrophoresis is continued until the non-incorporated dNTPs and primers have eluted from the matrix, after which the gel is optionally rinsed or washed and the products inside the matrix detected by an appropriate means for the label used. A combination of labels can be used in labelling primers so that different products (e.g., primer extension products of extended telomerase substrates and of a control nucleic acid) can be detected in a single well.

Streptavidin-coated microtiter well-plates (Boehringer Mannheim) can also be used for detection of amplified or non-amplified telomerase extension products. One illustrative method involves labelling the 5' end of a telomerase substrate with biotin, capturing the extended telomerase substrates in the streptavidin-coated microtiter well-plates, and detecting the presence of extended telomerase products by a labelled probe complementary to telomeric repeats. As noted above, the label can be a radioisotope or a fluorescent, phosphorescent, chemiluminescent, or enzymatic molecule, or any of various chromophores, epitopes or antigens. Of course, the reverse of this procedure, where the extended telomerase substrates are captured by a biotinylated return primer (e.g., $(CTR)_4$, CX, ACT, ACX, LC) and detected by a probe complementary to the extended telomerase substrate can also be used. The extended products can also be captured by capture probes bound to the plates that are complementary to the telomerase substrate or to telomeric repeats.

Extended products can also be captured by incorporating biotin-labelled dNTP (e.g., biotin-dUTP) during telomerase extension or product amplification and capturing the extended product in the streptavidin plate. The products are then detected by probe complementary to the telomerase substrate or to telomeric repeats.

Applications

Having this description of the method and reagents employed, one can consider applications for the telomerase assay of the present invention, which include research, diagnostic and other applications. Because the assay is fast, simple, and amenable to single reaction vessel reactions, the assay can be used in research and clinical laboratory settings where there is a need to detect telomerase-positive cells or samples. Such applications include, but are not limited to: (i) detection of immortal cells in tumor biopsies for the identification of potential cancer cells, before or after therapy; (ii) identification in a cell-based or cell-free screen of agents capable of activating, derepressing, inhibiting, or repressing telomerase, including immortalizing agents (e.g., oncogenes) or compounds that activate telomerase and extend telomeres and replicative lifespan of cells; (iii) identification in culture systems or in vivo of stem cells, early progenitor cells, or fetal cells that possess telomerase activity; (iv) examination of telomerase regulation during differentiation and development; (v) identification of telomerase-positive fractions generated during purification of telomerase; (vi) identification of protozoal or fungal infections; (vii) diagnosis of diseased states or medical conditions characterized by a different level of telomerase activity in a patient relative to an individual not having the diseased state or particular medical condition; and (viii) diagnosis of certain types of infertility characterized by an absence of telomerase activity.

The diagnostic methods of the present invention can be employed with any cell or tissue type of any origin and can be used to detect an immortal cell of any origin, provided the cell expresses telomerase activity. For human samples, the detection of immortal cells will typically be used to detect the presence of cancer cells of any of a wide variety of types, including without limitation, solid tumors and leukemias including: apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell carcinomas), histiocytic disorders, leukemia (e.g., B-cell, mixed-cell, null-cell, T-cell, T-cell chronic, HTLV-II associated, lymphocytic acute, lymphocytic chronic, mast-cell, and myeloid leukemias), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia.

In one aspect of the invention, telomerase activity is determined from a body fluid (e.g. urine, phlegm, sputum, saliva, blood), a fine needle aspirate or biopsy to diagnose cancer, such as urogenitory cancer, bladder cancer, lung cancer, and leukemia. Preferably, the cell sample is obtained by using a non-invasive method to collect a fluid sample and then isolating cells therefrom, for example, by centrifugation, filtration or other physical means. This simple method of obtaining cells for screening for different cancers is particularly suited to the clinical setting.

Telomerase activity can then be assayed, allowing for diagnosis based on the presence of telomerase activity. In the diagnostic methods of the invention, the assay will be conducted to determine whether an elevated level of telomerase is present. The phrase "elevated level" means that the absolute level of telomerase activity in the particular cell is elevated compared to normal somatic cells in that individual, or compared to normal somatic cells in other individuals not suffering from a disease condition. Generally, any detectable level of telomerase activity is considered elevated in cells from normal, postnatal human somatic tissue. Although telomerase activity is present in germline cells, and low levels of telomerase activity can be detected in stem cells and certain hematopoietic system cells, such cells do not present problems for the practitioner of the present method. Germline cells can be readily distinguished and/or separated from human somatic tissue samples, and the telomerase activity present in stem cells and certain hematopoietic cells is present at such low levels that the few such cells present in somatic tissue samples will not create false positive signals from a telomerase activity assay or can be detected and distinguished using other means. The detection of telomerase activity in somatic cells is indicative of the presence of immortal cells, such as certain types of cancer cells, and can be used to make that determination even when the cells would be classified as non-cancerous by pathology. Thus, the method of the present invention allows cancerous conditions to be detected with increased confidence before cells become visibly cancerous.

The diagnostic tests of the invention can also be carried out in conjunction with other diagnostic tests. In some instances, such combination tests can provide useful information regarding the progression of a disease, although the present method for testing for telomerase activity provides much useful information in that regard as well. When the present method is used to detect the presence of cancer cells in a patient sample, the presence of telomerase activity can be used to determine where a patient is at in the course of progression of the disease, whether a particular tumor is likely to invade adjoining tissue or metastasize to a distant location, and whether cancer is likely to recur or has recurred. Tests that may provide additional information in conjunction with the present method include diagnostic tests for DNA ploidy, fraction of cells in S-phase, nodal status, Her-2/neu gene products, p53, p16, p21, ras, and other oncogenes.

The level of telomerase activity can also be used to monitor the effectiveness of chemotherapeutics during cancer treatment. The level of telomerase can be a monitor of the effectiveness of a telomerase inhibitor or retinoid therapy, or any other cancer therapy, where telomerase activity is decreased through telomerase inhibition, cellular differentiation, or cell death, respectively. The level of telomerase can monitor the effectiveness of any oncolytic or tumor-debulking procedure by providing an estimate of the number of immortal cells within the patient.

Telomerase activity, or the presence of telomerase components, can also be determined as a marker for fetal cells, e.g., collected from cord or maternal blood. Identification of fetal cells in maternal blood is useful in diagnosing pregnancy or in the genetic testing of fetal cells, i.e., to identify the cells to be tested.

Telomerase activity can also be used as a marker for bone marrow proliferation. A bone marrow transplant is typically more successful when less differentiated bone marrow cells are employed. Because hematopoietic cells lose telomerase activity as they differentiate, the presence of telomerase activity can be used as a marker for hematopoietic cells useful for transplant purposes. Any of the current assays for telomerase activity, as well as assays that may be developed in the future can be used.

The present invention also provides kits for performing the diagnostic method of the invention. Such kits can be prepared from readily available materials and reagents and can come in a variety of embodiments. For example, such kits can comprise, in an amount sufficient for at least one assay, any one or more of the following materials: oligonucleotide telomerase substrates (e.g., TS), control reagents (e.g., control oligonucleotides (e.g., TSNT, TSR8), positive control extracts or cell pellets), and oligonucleotide primers (e.g., CX, ACT, ACX, LTS, CLT, LC, LG, NT), optionally provided together with any of the following: reaction vessels, buffers (e.g., cell lysis buffer, end-labelling buffer, TRAP reaction buffer), water (preferably RNase, DNase and protease-free), nucleotides, labels or stains (e.g., SYBR Green, fluorescer, labelled oligonucleotide probes, such as bDNA probes ), enzymes (e.g., RNA or DNA polymerase, ligase, RNase, polynucleotide kinase), other reagents necessary or helpful to perform the assay, and instructions. Typically, instructions include a tangible expression describing the reagent concentration or at least one assay method parameter, such as the relative amounts of reagent and sample to be admixed, maintenance time periods for reagent/sample admixtures, temperature, buffer conditions, and the like, to allow the user to carry out any one of the assays described above.

In one embodiment of the invention, the kit comprises a reaction tube in which is placed a telomerase substrate and a primer. A preferred form of this kit comprises such a tube in which the primer is separated from other reaction components by a wax barrier. The primer may be coated on or attached to a glass bead. A wide variety of kits and components can be prepared according to the present invention, depending upon the intended user of the kit and the particular needs of the user. Other formats utilize oligonucleotide primers, such as the ACX primer, that allow wax-free assay conditions.

The reagents of any diagnostic assay described herein can be provided in solution, as a liquid dispersion or as a substantially dry power, e.g., in lyophilized form, either independently or in a mixture of components to improve ease of use. Where an enzyme or other degradable reagent is provided, conditions are chosen so as to stabilize the reagents, e.g., storage at lower temperature, addition of stabilizing agents (e.g., glycerol or a reducing agent). Unstable reagents can be provided together with or separately from the more stable components of the kit. A solid support such as a multiwell plate, glass beads, or tubes, and one or more buffers can also be included as separately packaged elements in a kit. The kits discussed herein in relation to diagnostic methods or research applications are similar in a general sense to those customarily utilized in diagnostic systems and so can include glass and plastic (e.g., polyethylene, polypropylene and polycarbonate) bottles, vials, plastic and plastic-foil laminated envelopes, and the like.

The following examples describe specific aspects of the invention to illustrate the invention and provide a description of the present method for those of skill in the art. The examples should not be construed as limiting the invention, as the examples merely provide specific methodology useful in understanding and practice of the invention.

EXAMPLE 1

Preparation of CHAPS-Extracted Telomerase

In this Example, cell extracts prepared using the zwitterionic detergent-based extraction method of the invention were tested for telomerase activity using the conventional telomerase assay.

The cell extracts were prepared from immortal 293 cells, which are known to express telomerase activity and are derived from human embryonic kidney cells transformed with fragments of adenovirus type 5 DNA. The cells were grown in Joklik's medium containing 5% to 10% fetal bovine serum and then collected by centrifugation (unless otherwise noted, the procedure below assumes that about $1 \times 10^6$ cells were collected), washed once in PBS, pelleted at 10,000×g for 1 minute at 4° C., and resuspended in 1 ml of ice-cold PBS. The cells were pelleted again and resuspended in ice-cold lysis buffer [10 mM Tris-HCl (pH 7.5), 1 mM $MgCl_2$, 1 mM EGTA, 0.1 mM PMSF (benzamidine or AEBSF can also be used), 5 mM β-mercaptoethanol, DEPC-treated water, 0.5% CHAPS (from Pierce), 10% glycerol] at a concentration of 20 µl of lysis buffer per $10^4$–$10^6$ cells (depending on the purpose of the experiment). The suspension was incubated on ice for 30 minutes and then spun in a microultracentrifuge at 10,000×g for 30 minutes at 4° C. The supernatant was removed to another tube, quick-frozen on dry ice, and optionally stored until use at −70° C. These extracts typically contained a total protein concentration of 5 to 10 mg/ml, and the telomerase activity was stable to multiple freeze-thaws.

The procedure for and conditions of the conventional telomerase assay were as described by Counter et al., 1992; Counter et al., 1994, *EMBO J.* 11:1921–1929; and Counter et al., 1994, *J. Virol.* 68:3410–3414, using oligonucleotide substrates at a concentration of 1 µM. See also Morin, 1989, *Cell* 59:521–529. The products were separated on an 8% polyacrylamide sequencing gel and exposed overnight to a Phosphorimager™ screen (Molecular Dynamics, Sunnyvale, Calif.). The telomerase substrates used in the conventional assay were 5'-GTTAGGGTTAGGGGTTAGG-3' (abbreviated as "(GTTAGG)$_3$"; SEQ ID NO:15); 5'-TTAGGGTTAGGGTTAGGG-3' (abbreviated as "(TTAGGG)$_3$"; SEQ ID NO:16), and 5'-AATCCGTCGAGCAGAGTT-3' (abbreviated as "TS"; SEQ ID NO:3). Control samples were also assayed, which contained extracts pretreated with RNase by incubation of 10 µl of extract with 0.5 µg of RNase (DNase-free, Boehringer Mannheim) for 10 minutes at 25° C., which degrades the RNA component of telomerase and abolishes activity. Telomerase pauses after adding the first G of the G triplet, so the number of nucleotides added before the first pause (and thus the phasing of the ladder) is five for (GTTAGG)$_3$ (SEQ ID NO:15), four for (TTAGGG)$_3$ (SEQ ID NO:16), and two for the TS oligonucleotide.

The results demonstrated that the CHAPS-extracted telomerase activity functioned as predicted for human telomerase. The detergent-extracted activity produces a six nucleotide ladder of extension products characteristic of telomerase activity. A shift in product phase is observed dependent upon the 3'-sequence of the oligonucleotide telomerase substrate, as is expected for telomerase-mediated extension, and the extracted telomerase can extend a non-telomeric oligonucleotide previously shown to be a telomerase substrate (Morin, 1991, *Nature* 353:454–456) with 5'-TTAGGG-3' repeats (as confirmed using dideoxynucleotide chain termination sequencing). The activity was abolished by RNase treatment, as would be expected for telomerase activity (Greider and Blackburn, 1985, *Cell* 43:405–413; Greider and Blackburn, 1989, *Nature* 337:331–337; Morin, 1989, *Cell* 59:521–529).

EXAMPLE 2

PCR Amplification of Telomerase Extension Products

This example illustrates the telomerase assay method of the present invention in which a DNA polymerase is used to mediate the primer extension reaction in a polymerase chain reaction. The reaction components include the telomerase substrate TS (the sequence of which is provided in Example 1, above), which telomerase extends by synthesizing telomeric repeats and which also functions as the upstream primer in the PCR step, and the downstream primer CX, the structure of which is defined by its sequence 5'-(CCCTTA)$_3$CCCTAA-3' (SEQ ID NO:1). Mismatches were designed in the CX primer/extended telomerase substrate to reduce interaction between the CX primer and unextended TS oligonucleotide telomerase substrate and so minimize primer-dimer (more accurately CX primer/TS dimer formation).

As noted above, telomerase is known to extend oligonucleotides of non-telomeric sequence, such as the TS oligonucleotide (Morin, 1991, *Nature* 353:454–456), and oligonucleotide substrate TS was used to avoid non-specific amplification due to PCR primer complementarity. As further modifications to avoid primer interaction, mismatches (relative to TS) in the downstream primer CX, single stranded binding protein T4 gene 32 protein, hot start PCR, and an annealing temperature of 50° C. were used to conduct the telomerase activity assays described in this Example. Under these conditions, specific amplification occurs only if the oligonucleotide substrate has been extended with three or more 5'-TTAGGG-3' repeats, resulting in a six nucleotide ladder of TRAP assay products extending from 40 nucleotides (the first amplifiable telomerase product) up to the limit of gel resolution.

Yet another important modification that greatly improves the ease and efficiency of the present method relates to the development of a novel reaction buffer in which both telomerase and DNA polymerase can function. Use of this buffer allows one to employ a single tube set-up or format for the TRAP assay. This modification allows one to increase the specificity of primer extension, because the CX primer is initially separated from the rest of the reaction mix by a wax barrier, which melts only at the higher temperatures that mediate stringent hybridization conditions. The assay tubes were prepared by adding 2 µl of a 50 ng/µl suspension of CX primer (0.1 µg), which was spun to the bottom of the tube and evaporated until dry in a Speed-Vac™ centrifuge.

A trace amount of bromophenol blue was added to the CX primer suspension to monitor possible leakage through the wax barrier prior to thermal cycling. While the addition of dye for this purpose is in no way required for practice of the present invention, dye addition can be a convenient method for monitoring the integrity of a manufacturing process. Tubes were then heated at 70° C., and 7–10 µl of molten wax (Ampliwax™, Perkin-Elmer) was pipetted into the bottom of the tube. After the wax was allowed to solidify at room temperature, the tubes were stored at 4° C. Tubes were warmed to room temperature before use. No effect on assay performance was observed using prepared tubes stored at 4° C. for up to two months; the expected shelf-life of such tubes (and kits comprising the same) is expected to be at least a year.

Reactions were typically carried out by the addition of 50 µl of TRAP reaction solution above the wax barrier. The reaction solution contained 20 mM Tris-HCl, pH 8.3, 1.5 mM MgCl$_2$, 63 mM KCl, 0.005% Tween 20, 1 mM EGTA, 50 mM each dNTP, 0.1 µg of TS oligonucleotide, 0.5 mM T4 gene 32 protein, 0.1 mg/ml BSA, 2 Units of Taq DNA polymerase (optionally use 2 Units of Taq treated with an equal volume of TaqStart™ antibody from Clontech to enforce hot start PCR), and 1–2 µl of a CHAPS cell extract. For radiolabelling of products, 0.2 to 0.4 µl of 10 µCi/µl $^{32}$P-dGTP and/or $^{32}$P-dCTP (3000 Ci/mmol) was added to the reaction. After 10 minutes at 20° C. for extension of oligonucleotide TS by telomerase, the tubes were transferred to the thermal cycler (96 well Singleblock™ system, Ericomp) for 27 cycles, each cycle comprising incubation temperatures and periods of 94° C. for 30 seconds, 50° C. for 30 seconds, and 72° C. for 30 seconds to 1.5 minutes The CX primer (0.1 µg) was liberated when the wax barrier melted at ~70° C. Those of skill in the art will recognize that the reaction times, temperatures, and buffers described in this Example can vary, depending upon the needs of the practitioner, the particular substrates and primers employed, and the source of the extract and DNA polymerase (see Example 4).

For instance, the telomerase extension reaction can be conducted at temperatures ranging from about 10° C. to about 42° C., depending upon the source of the telomerase. The telomerase reaction time can vary widely, depending upon the number of primer extension steps employed, the amount of telomerase expected to be in the sample, and the time available to the practitioner. Typically, the telomerase reaction time will be between 5 and 60 minutes, but the time could be up to several hours. In similar fashion, the PCR cycles can be composed of cycle times and temperatures that vary widely. The simplest PCR cycle comprises a duplex nucleic acid denaturation step followed by a primer annealing and extension step. While denaturation is typically carried out by heating the reaction mixture, other methods, such as helicase treatment, can be used, and the heating method itself can be conducted at a wide range of temperature for any amount of time sufficient to denature but not damage the DNA. In similar fashion, the time and temperature of the primer annealing step depends to a great extent on the reaction buffer and primer sequence, concentration, and composition, as well as the specificity required by the practitioner, while the time and temperature of the primer extension step depends greatly upon the type of DNA polymerase employed. Those of skill in the art will recognize and understand that the present invention is not limited by the times, temperatures, and variations in buffer and other reaction components that can be employed in the method.

For analysis of the samples, one half of the reaction mixture was analyzed by electrophoresis in 0.5×TBE on 15% polyacrylamide non-denaturing gels. Visualization of the products was by ethidium bromide staining, silver staining, SYBR™ Green staining (Molecular Probes) autoradiography, or Phosphorimager™ analysis (Molecular Dynamics, Sunnyvale, Calif.) of the gels. Control samples were assayed, using: a sample from which the TS oligonucleotide was omitted; a sample from which the cell extract was omitted; a TRAP assay sample of an immortal 293 cell extract; a sample of 293 extract pretreated by incubation for 10 minutes at 65° C. to heat-inactivate the telomerase; a sample of 293 extract pretreated by incubation for 10 minutes with 0.5 µg of RNase (DNase-free, Boehringer Mannheim) at 25° C. to destroy the RNA component of telomerase; a sample of phenol-extracted 293 extract (by mixing in an equal volume of a 1:1 phenol:chloroform mixture, vortexing for 30 seconds, centrifuging to separate the phases, and collecting the aqueous phase); a sample of 293 extract pretreated with protease by incubation of the extract (50 µl) with 5 µg of Bromelain protease (Boehringer Mannheim) for 10 minutes at 37° C., removal of the Bromelin protease by incubation with an equal volume of carrier-fixed α2-macroglobulin (Boehringer Mannheim) for 30 minutes at 25° C. with shaking and then centrifugation (to pellet the α2-macroglobulin/Bromelain complex) for 10 minutes at 10,000×g, and collection of the supernatant for analysis; a normal fibroblast BJ cell extract, which should lack telomerase activity; and a cell extract enriched for telomerase by DEAE chromatography (Morin, 1991, *Nature* 353:454–456).

The results of these multiple control experiments demonstrate that a positive signal in the TRAP (Telomerase Repeat Amplification Protocol) assay requires a ribonucleoprotein in an immortal cell extract capable of extending the TS oligonucleotide with two or more 5'-TTAGGG-3' repeats, validating the assay for specific detection of telomerase activity.

To examine more closely the sensitivity of the TRAP assay, another set of assays was conducted to test the limits of detergent extraction and TRAP detection under the conditions employed. For extraction of different numbers of cells, the volume of lysis buffer was kept constant at 100 µl. No activity was observed in an assay of about $10^5$ cell equivalents from an extract of $10^7$ normal fibroblast BJ cells, as indicated by the absence of the ladder of bands. Telomerase activity was observed in an assay of about $10^4$ cell equivalents from an extract of $10^6$ immortal 293 cells, in an assay of about $10^3$ cell equivalents from an extract of $10^5$ 293 cells, and in an assay of about $10^2$ cell equivalents from an extract of $10^4$ 293 cells. No activity was observed in an assay of about 10 cell equivalents from an extract of $10^3$ 293 cells or in a control assay with lysis buffer only.

The limit of telomerase detection in $10^2$ cells was confirmed by TRAP assays of serial dilutions of an extract from $10^6$ 293 cells. This limit is a function of the TRAP assay conditions employed and should be considered a practical limit under the given set of conditions rather than an absolute limit of the sensitivity of the current method. Example 15 is an illustrative example describing the detection of telomerase activity in a single cell. Those of skill in the art will recognize that other means of increasing the sensitivity of the assay are available. For instance, use of primers CTR3 [(5'-CCCTAA-3')$_3$ (SEQ ID NO:17)] or CTR4 [(5'-CCCTAA-3')$_4$ (SEQ ID NO:18)] instead of CX further increases sensitivity, although these primers are more likely to interact with the unextended TS primer. The limit of sensitivity was also analyzed by titration of the synthetic telomerase product TS+4 (which contains oligonucleotide TS followed by four telomeric repeats). Dilutions of TS+4 oligonucleotide were mixed with heat-treated (telomerase inactivated) 293 extract and analyzed in TRAP assays. In this analysis, the assay gave a clear positive signal from $10^6$ molecules of TS+4. In addition, telomerase activity from mouse tissue (telomerase activity is present in somatic cells of mice) and cell extracts was detected by TRAP assay even though the mouse telomerase by conventional assay was shown to be mostly non-processive (i.e., adds only a single repeat; Prowse et al., 1993, *Proc. Natl. Acad. Sci. USA* 90:1493–1497), indicating that the TRAP assay is detecting very low levels of processive mouse telomerase activity that cannot be visualized by the conventional assay or mouse telomerase is more processive under TRAP conditions.

For the convenience of the practitioner, the following product information is provided. Reaction tubes were 0.2 ml Strip-ease™ tubes from Robbins Scientific (Sunnyvale, Calif.) and were autoclaved before use. All oligodeoxyribonucleotides were Ultrapure grade (HPLC-purified) obtained from Keystone Laboratory (Menlo Park, Calif.) and were suspended in DEPC-treated H$_2$O or TE buffer (10 mM Tris.Cl, pH 7.6; 1 mM EDTA, pH 8.0) at a concentration of 1 mg/ml. Taq DNA polymerase, Tween 20, and T4 gene 32 protein were purchased from Boehringer Mannheim. Radioisotopes were purchased from NEN-Dupont. The dNTPs were purchased from Pharmacia and were aliquoted, stored at −20° C., and thawed (no more than twice) before use. All other reaction components were molecular biology grade and purchased from Sigma, except when otherwise noted. Diethylpyrocarbonate (DEPC)-treated, de-ionized, sterile H$_2$O was used routinely.

EXAMPLE 3

Relative Sensitivity of TRAP and Conventional Telomerase Assays—Assay of Telomerase Activity in Normal Somatic and Immortal Cells This Example describes telomerase assays conducted on cell samples of immortal cell lines and normal somatic cell cultures from different tissues and individuals. Adherent cell cultures, such as BJ cells, a normal somatic cell culture of human skin fibroblasts, were grown to 80% confluency prior to extract preparation. The assays ($10^5$ cell equivalents per reaction) were conducted as described in Examples 1 and 2, above, and the results of the assay are summarized in Table 1, below. Assays were performed on the same 10 cell extracts, which were prepared using the CHAPS detergent lysis method (see Examples 1 and 2, above).

Control samples were assayed with extracts pretreated with RNase, which should eliminate any telomerase activity in the sample. The breast carcinoma line MCF-7/ADR-RES, pancreatic carcinoma line AsPC-1, prostatic carcinoma line PC-3, melanoma line M14, normal foreskin fibroblast cell culture BJ, lung carcinoma line NCI-H23, normal stromal fibroblast cell culture 31YO, normal lung fibroblast cell culture IMR-90, ovarian carcinoma line OVCAR-3, colon carcinoma line COLO205, and immortal kidney cell line 293 were assayed. For conventional assays, $10^6$ cell equivalents were used per reaction.

Some immortal cell lines (293, MCF-7/ADR-RES, NCI-H23, OVCAR-3, COLO205, M14) showed activity in both assays, others (AsPC-1 and PC-3) showed activity only in the TRAP assay, and the normal somatic cell cultures (BJ, IMR-90 and 31YO) showed no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1, below. Each dividing cell culture was detergent-extracted and tested for telomerase activity using the TRAP assay. The specific immortal cell lines and normal somatic cell cultures are listed by tissue of origin. Immortal cell lines and normal somatic cell cultures tested were: (1) Skin—melanoma (LOXIMVI, M14, Malme-3M, UACC-62), normal fibroblasts (GFS, S37b, Malme-3, BJ), normal keratinocytes (primary foreskin); (2) Connective—Fibrosarcoma (HT-1080); (3) Adipose—liposarcoma (SW872); (4) Breast—adenocarcinoma (MCF7, MCF-7/ADR-RES, MDA-MB-231), ductal carcinoma (T 47 D, MDA-MB-435), carcinoma (MDA-MB-157, MDA-MB-175-VI, MDA-MB-436, MDA-MB-468, ZR-75-1, ZR-75-30, UACC-812, UACC-893, BT-20, BT-474, BT-483, BT-549, HS578T, SK-BR-3, SCC70, SCC38, SCC202), normal epithelial and stromal cells (HME: 15, 17, 31, 32, 35); (5) Lung—carcinoma (NCI-H522, NCI-H23, A549, EKVK, 1299, H146, H69, NCI-H460, H358, H182), SV40 T-antigen transformed (IDH4, SW26-IG, SW-26-C4), normal fetal fibroblasts (GFL, IMR-90, Wi38); (6) Stomach—gastric carcinoma (KATO-III); (7) Pancreas—ductal carcinoma (SU.86.86), adenocarcinoma (AsPC-1, Capan-1); (8) Ovary—carcinoma (OVCAR-3, OVCAR-5, IGROV-1), adenocarcinoma (OVCAR-8); (9) Cervix—carcinoma (HeLa S3, C-33 A, HT-3), normal primary epithelial cells; (10) Uterus—normal primary endometrial cells; (11) Kidney—carcinoma (A498, CAKI-1), Ad5-transformed embryonic kidney cells (293); (12) Bladder—carcinoma (5637), transitional cell carcinoma (T24), squamous carcinoma (SCaBER), normal fetal (FHs 738B1); (13) Colon—adenocarcinoma (COLO 205, SW-620, HCT-116); (14) Prostate—adenocarcinoma (PC-3, DU 145), SV40 transformed BPH fibroblasts (BPH-1), normal stromal fibroblasts (31YO), BPH fibroblasts (S52); (15) CNS—carcinoma (U251, SNB-75), glioblastoma (SF268); (16) Blood—leukemia (Molt4, HEL), T-cell leukemia (Jurkats), acute promyelocytic leukemia (HL-60), chronic myelogenous leukemia (K-562), histiocytic lymphoma (U-937); (17) Retina—SV40 transformed pigmented epithelium (AGO6096A); and (18) Joint: normal synovial fibroblast (HSF).

TABLE 1

Telomerase Activity in Mortal and Immortal Cells

| Tissue of Origin | Cell Type (Tumor/Transformed/ Normal/) | Telomerase Activity (# positive/ # tested) |
|---|---|---|
| Skin | Tumor | 4/4 |
| | Normal | 0/5 |
| Connective | Tumor | 1/1 |
| Joint | Normal | 0/1 |
| Adipose | Tumor | 1/1 |
| Breast | Tumor | 22/22 |
| | Normal | 0/8 |
| Lung | Tumor | 10/10 |
| | Transformed | 2/3 |
| | Normal | 0/3 |
| Stomach | Tumor | 1/1 |
| Pancreas | Tumor | 3/3 |
| Ovary | Tumor | 4/4 |
| Cervix | Tumor | 3/3 |
| | Normal | 0/1 |
| Uterus | Normal | 0/1 |
| Kidney | Tumor | 2/2 |
| | Transformed | 1/1 |
| Bladder | Tumor | 3/3 |
| | Normal | 0/1 |
| Colon | Tumor | 3/3 |
| Prostate | Tumor | 2/2 |
| | Transformed | 0/1 |
| | Normal | 0/2 |
| CNS | Tumor | 3/3 |
| Retina | Transformed | 1/1 |
| Blood | Tumor | 6/6 |

None of the normal somatic cell cultures displayed detectable telomerase activity in the TRAP assay. Of the 74 immortal cell lines, 68 were tumor-derived lines and 6 were cell lines transformed with viral oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells will not replicate indefinitely.

EXAMPLE 4

Standard Operating Procedure for Telomeric Repeat Amplification Protocol (TRAP)

This Example provides a step-by-step protocol for performing the TRAP assay of the invention, in five parts: (A) Work station set-up; (B) Precautions; (C) Micro-extraction; (D) Quantitative Assay; and (E) Analysis. The method described provides for a quantitative analysis of the activity, and while a number of recommendations are made, those of skill will recognize that, depending on the conditions used and nature of the results desired, not all recommendations need be followed in all circumstances.

(A) Work Station Set-up

An important factor in the set-up of the TRAP assay is the environment where the initial reaction mixtures are made prior to the PCR step. The ideal environment is free of contaminating ribonucleases and PCR amplified DNA products, which can cause erroneous negative and positive results, respectively. A major source of PCR product (and RNase) contamination can be the person performing the experiment, who should maintain high standards of personal hygiene and avoid generation of aerosols of PCR products when opening or pipetting PCR products or disposing of gel buffer after the electrophoresis of PCR products. A positive air displacement hood, which blows in filtered air over the sample toward the investigator, is ideal. Separate solutions, pipettes, tubes, and tips should always be used and kept inside the hood. Work space should be wiped with 10% bleach prior to set-up of the reaction, and the hood should be routinely UV-irradiated when not in use. Also, barrels of pipettes should be periodically soaked in 10% bleach, even when aerosol-resistant tips are used. The investigator should wear gloves and a disposable lab coat with elastic wrist straps; the lab coat should be periodically changed.

A dedicated work area for setting up TRAP reaction can be prepared by placing an acrylic shield of 45.7 cm (L)×30.5 cm (W)×61 cm (H) size from VWR (cat. #56615-848) on a standard cubby-hole type desk. The top of the desk is covered either by a board or heavy cloth, and the front is blocked by the shield. This arrangement creates dead-air space, where the contaminants are prevented from falling into the working area from outside and the samples are physically blocked from the investigator. All the solutions, pipettes, tips, and tubes are kept inside the station, and the working area is routinely UV irradiated by a short-wave UV lamp mounted on the top of the station (Black Ray UV lamp, XX-15S, VWR cat #36575-059).

(B) Precautions

As noted above, and because the TRAP assay incorporates both PCR amplification and use of in vitro activity of a ribonucleoprotein (telomerase), there is a need for extreme caution to prevent PCR-product contamination (DNA) and RNase contamination, both of which can be detrimental to the assay. The following basic precautions can be followed in all steps of the assay protocol, including the telomerase extraction and PCR amplification steps, to avoid problems: (1) use DEPC-treated $H_2O$ for all solutions, or commercially available nuclease free water (Sigma) and aliquot the solutions in small amounts before use; (2) keep the assay solutions (PCR buffer, CHAPS extraction buffers, dNTPs, Taq polymerase, etc.) separate from other reagents in the laboratory; (3) wear gloves; (4) use a dedicated set of pipettors for the assay and aerosol-resistant tips (ARTs); and (5) do not analyze the amplified samples in the same area where the samples are prepared (i.e., do not open PCR tubes after the PCR amplification on the same bench where the assay reagents and pipettes/tips are located; instead use other pipettors (optionally without ARTs) at a location away from the PCR bench).

(C) Micro-extraction

The material requirements for the lysis buffer used in the micro-extraction procedure are shown below.

| Lysis Buffer (0.5% CHAPS or CHAPSO) | | | |
|---|---|---|---|
| Stock | Final | 0.5 mL | 10 mL |
| 1M Tris-HCT pH 7.5 | 10 mM | 5 µl | 100 µl |
| 1M MgCl$_2$ | 1 mM | 0.5 µl | 10 µl |
| 0.5M EGTA | 1 mM | 1 µl | 20 µl |
| *0.1M benzamidine | 0.1 mM | 0.5 µl | 10 µl |
| *βME(14.4M) | 5 mM | 0.17 µl | 3.5 µl |
| 10% (w/v) CHAPS or CHAPSO Detergent | 0.5% (w/v) | 25 µl | 500 µl |

-continued

| Lysis Buffer (0.5% CHAPS or CHAPSO) | | | |
|---|---|---|---|
| Stock | Final | 0.5 mL | 10 mL |
| 100% Glycerol | 10% (v/v) | 50 µl | 1 ml |
| DEPC H$_2$O | | 417.83 µl | 8.36 ml |

*0.1M benzamidine (1 µl) and beta-mercaptoethanol (0.35 µl) are added to 1 ml of lysis buffer just prior to performing the extraction step; PMSF or AEBSF can be used in place of benzamidine.

The micro-extraction procedure involves the following steps:

1. Establish cell number by counting or by extrapolation from tissue weight.
2. Pellet the cells or tissue, wash twice in PBS (Ca and Mg-free), repellet, and remove PBS. Cells or tissue can be stored at −80° C. at this point.
3. Resuspend cell pellet in 200 µl of lysis buffer per $10^6$–$10^5$ cells (depending on the application). For tissues, 200 µl of lysis buffer is used for 20–100 mg of tissue. Tissues can be treated by any of the following (a, b or c) methods.
   a) Soft tissues are homogenized using a motorized disposable pestle (VWR cat. #KT749520-0000, KT749540-0000). Firstly, the tissue sample is minced with a sterile blade until a smooth consistency is reached. The sample is transferred to a sterile 1.5 ml centrifuge tube and lysis buffer is added. Then the sample is homogenized with a motorized pestle on ice (~10 sec) until a uniform consistency is achieved.
   b) Connective tissue is placed in a sterile mortar and frozen by the addition of liquid nitrogen. The sample is then pulverized by grinding with a matching pestle. The thawed sample is then transferred to a sterile 1.5 ml centrifuge tube and resuspended in lysis buffer.
   c) Connective tissue is mixed with lysis buffer and the mixture is homogenized using a mechanical homogenizer (e.g., PowerGen™ Model 35 Homogenizer, Fisher, cat #15-338-35H) on ice until uniform consistency is achieved (~5 sec). Homogenization of the sample on ice prevents the sample from heating up which would potentially destabilize proteins.
4. Incubate the cells or treated tissue on ice for 30 minutes.
5. Spin the cells or treated tissue in a microcentrifuge (Eppendorf) at 12,000 g for 30 minutes at 4° C.
6. Remove extract to another tube and use 1 to 2 µl per TRAP assay; one can quick-freeze the remainder on dry-ice and store at −70° C., if desired. Typical protein concentrations are between 1 and 10 µl.

(D) Quantitative Assay

The following materials are recommended for the assay: TS primer (5'-AATCCGTCGAGCAGAGTT-3'; SEQ ID NO:3; HPLC purified, 1 µl); ACX primer (5'-GCGCGG[CTTACC]$_3$CTAACC-3'; SEQ ID NO:4; HPLC purified, 0.1 µl); NT primer (5'-ATCGCTTCTCGGCCTTTT-3'; SEQ ID NO:6; HBPLC purified, 0.1 µl); TSNT internal control (5'-AATCCGTCGAGCAGAGTTAAAAGGCCGAG-AAGCGAT-3'; SEQ ID NO:5; HPLC purified, 0.01 amol/µl); TSR8 quantitation standard (5'-AATCCGTCGAGCAGAGTTAG[GGTTAG]$_7$-3'; SEQ ID NO:19; HPLC purified, 1 amol/µl); 2.5 mM dNTPs (Pharmacia); Taq DNA polymerase (Perkin Elmer; AmpliTaq™); and 10×TRAP Buffer.

| 10X TRAP Buffer | |
| --- | --- |
| Components | For 5 ml |
| 200 mM Tris-HCl, pH 8.3 | 1 ml (1M Tris-Cl pH 8.3) |
| 15 mM MgCl2 | 75 μl (1M MgCl$_2$) |
| 630 mM KCl | 3.15 ml (1M KCl) |
| 0.5% Tween 20 | 250 μl (10%, Boehringer Mannheim) |
| 10 mM EGTA | 250 μl (0.2M EGTA) |
| 1 mg/ml BSA | 250 μl (20 mg/ml) (Boehringer Mannheim, Fraction V) |
| water (protease, RNase, and DNase-free) | 25 μl |

For a quantitative assay, one can use an end-labelled TS substrate, in which case, the substrate/primer can be end-labelled with [$^{32}$P]γATP using the reaction mixture described below, or with other reagents, such as 5'-biotin, digoxigenin, fluorescein or another fluorophore, depending on the particular detection and quantitation system to be employed:

| End-Labelling Reaction Mixture | |
| --- | --- |
| [$^{32}$P]γATP (3000 Ci/mmol, 10 μCi/μl) | 2.5 μl |
| TS primer (1 μg/μl) | 1.0 μl |
| 10 x OPA buffer (Pharmacia) | 1.0 μl |
| T4 polynucleotide kinase (9.7 U/μl) | 0.5 μl |
| DEPC water | 5.0 μl |

The end-labelling reagents are combined in a reaction vessel and incubated for 20 minutes at 37° C., followed by 5 minutes at 95° C. It will be apparent to the artisan that the end-labelling conditions (such as amount of radioactive nucleotide or oligonucleotide) can be varied depending on the particular application and needs of the practitioner. For example, increased sensitivity of the assay can be achieved by increasing the specific activity of the labelled primer, as described in Example 15.

To prepare a telomerase assay reaction mixture, the following materials are mixed in a PCR reaction tube.

| Material | For 50 μl Total Volume |
| --- | --- |
| 10X TRAP Buffer | 5 μl |
| 2.5 mM dNTPs (Pharmacia) | 1 μl |
| End-labelled primer (0.1 μg/μl TS) | 1 μl |
| ACX primer (0.1 μg/μl) | 1 μl |
| NT primer (0.1 μg/μl) | 1 μl |
| TSNT internal control (0.01 amol/μl) | 1 μl |
| Taq polymerase (AmpliTaq ™, Perkin Elmer) | 0.4 μl (2 Units) |
| DEPC treated H$_2$O | 37.6 μl |
| Telomerase Extract | 2 μl |

Optional components include 0.2 μl of T4 gene 32 protein (5 mg/ml, available from Boehringer Mannheim), and 0.4 μl of TaqStart™ antibody (available from Clontech; the polymerase is mixed with the antibody prior to the assay).

Controls

In the above reaction mixture, the telomerase extract can be replaced with one of the following: a negative control RNase-inactivated or heat-inactivated extract (extract is heat-inactivated by incubation at 75° C.–85° C. for 10 minutes); positive control cell extract; CHAPS lysis buffer (primer-dimer/PCR contamination control); and TSR8 (0.1 amol quantitation control).

The reaction is carried out according to the following steps:

1. Incubate the reaction mixture at 30° C. for 10 minutes (this step can be performed in the same instrument used to perform step 2);
2. Incubate the reaction mixture at the following temperatures for the times indicated to conduct the PCR: 94° C. for 30 seconds, then 60° C. for 30 seconds; repeat for 25–30 cycles;
3. Add loading dye containing bromophenol blue and xylene cyanol (0.25% each in 50% glycerol/50 mM EDTA), and subject samples to 10–15%, preferably 12.5%, nondenaturing PAGE in 0.5×TBE, until the bromophenol blue runs off the gel (molecular marker V from Boehringer Mannheim is a good DNA marker for this gel); and
4. Visualize product formation, e.g., by Phosphorimager™ screen (for a radioactive label) or another appropriate means of detection.

The presence of the TSNT internal control results in a specific PCR amplification product that appears as a band on a gel 14 bp below the first products of the TRAP assay, regardless of RNase treatment or no extract control. The internal control band can be used to normalize the PCR amplifications from different samples, and to calculate the number of telomerase products generated when used in combination with end-labelled TS oligonucleotide substrate/primer as described below.

(E) analysis
  i) Measure the signal of the region of the gel lane corresponding to the TRAP product ladder bands from all samples including non-heat-treated (x) and heat-treated sample extracts ($x_o$), CHAPS lysis buffer only control ($r_o$), and TSR8 quantitation control (r);
  ii) Measure the signal from the TSNT internal standard in non-heat-treated samples (c) and TSR8 quantitation control ($c_R$).
  iii) Quantitate the amount of telomerase product using the following formula:

$$TPG \text{ (units)} \frac{(x - x_o)/c}{(r - r_o)/c_R} \times 100 \text{ (if 1}\mu\text{l (0.1 } a\text{mol) of } TSR8 \text{ is used)}$$

Each unit of TPG (Total Product Generated) corresponds to the numbers of TS primers (in 1×10$^{-3}$ amole or 600 molecules) extended with at least 3 or 4 or more telomeric repeats by telomerase in the extract. Typically, the assay has a linear range of 1 to 1000 TPG, which is equivalent to telomerase activity from approximately 10 to 10,000 control cells in a 10 minute incubation at 30° C.

This calculation is valid only if the TS substrate is end-labelled and does not apply to a TRAP protocol in which direct incorporation of radioactive dNTPs or non-radioactive quantitation is used for detection, because the signal would depend on the length of the products in that case. The primers should be present in excess over templates for the quantitative analysis to be accurate. Therefore, if a sample has very high levels of telomerase activity, one can dilute the extract so that the PCR primers are not limiting.

Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products.

EXAMPLE 5

In Situ Detection of Telomerase Activity

This example illustrates the telomerase assay method of the present invention when applied in situ. The method involves internalization of a telomerase substrate by cells and detection of the extended telomerase substrate if telomerase is present in the cells. Those of skill in the art will recognize that numerous methods are available for internalization of nucleic acids by cells and, in light of the present specification, a variety of methods can be used for the detection of extended telomerase substrate. There is no limitation as to which telomerase substrate is used other than that imparted by the particular detection method used. In one embodiment, a plasmid telomerase substrate is used. A preferred plasmid telomerase substrate is a selectable, multicopy vector having a mammalian origin of replication, which vector comprises a non-telomeric telomerase substrate sequence (e.g., TS sequence, 5'-AATCCGTCGAGCAGAGTT-3') (SEQ ID NO:3) adjacent to a restriction site (e.g., Isce I) that is not present in the mammalian genome. In this embodiment, the restriction endonuclease specific for the restriction site is supplied to provide a linearized telomerase substrate. For example, a second plasmid containing the gene coding for the specific restriction enzyme (e.g., Isce I), operably linked to an inducible promoter, is coinfected with the first plasmid into the target cells. Upon induction, the plasmid encoding the unique restriction enzyme expresses the restriction enzyme that cleaves the specific restriction site present on the insert of the telomerase substrate plasmid. This results in a linearized telomerase substrate plasmid that can be elongated with TTAGGG repeats by telomerase.

A. Internalization of DNA substrate

Internalization of the substrates can be achieved using passive internalization (e.g., target oligonucleotides or DNA added to the cell media at a concentration of 10–100 $\mu$M), microporation by a detergent or Staphylococcus alpha toxins (BRL, following the manufacturer's conditions), liposomes (e.g., LipofectAmine™, Lipofectin™, LipofectAce™, from BRL, following the manufacturer's conditions), or electroporation (e.g., in DMEM media with total volume of 0.8 ml, V=0.25 KV, Capacitance=960 $\mu$F, with no resistance in a electroporation cuvette with 0.4 cm gap). After the target nucleic acid is internalized by the cells, the cells are incubated at 37° C. for 1–6 hours. For solid tissue samples, frozen non-fixed tissue is cut into a thin section on a cryostat, placed on a clean sterile microscopic glass slide and incubated at 37° C. with media containing DNA telomerase substrate, or DNA telomerase substrate incorporated into liposomes, for 1–6 hours. After the incubation, the tissue is gently washed with PBS, and fixed using the methods discussed below. If active telomerase is present, the DNA substrate will be extended with de novo synthesis of TTAGGG repeats.

B. Sample fixation and permeabilization

After substrate internalization and incubation, the cells or sectioned tissues are treated to stop the telomerase reaction and any degradative process and permeabilized to allow for detection. For example, the samples can be washed or rinsed twice with PBS and fixed by any of various methods known in the art, such as with MeOH:Acetic acid (3:1 ratio, incubated overnight at −20° C.), with buffered 10% formalin (4–15 hr at room temperature), with 3% paraformaldehyde (4–15 hr at room temperature), with 4% formaldehyde (4–15 hr at room temperature), or with a commercially available fixative such as Permeafix (ORTHO, 1–5 hr at room temperature) can be used. The cells are then fixed onto a microscopic glass slide by Cytospin™ (Shandon) and dried overnight at room temperature. The fixed samples are then permeabilized by a protease treatment (e.g., proteinase K, pronase, trypsin, pepsin [2 mg/ml]) for 10–60 minutes at room temperature. The samples can then be washed or rinsed with PBS at room temperature for 10 min, washed briefly with 100% EtOH, and air dried.

C. Detection of extended telomerase

After permeabilization of the samples, the extended telomerase substrate, if present, can be detected by various means. In one aspect of the present invention, PCR detection is used. Various in situ PCR conditions using illustrative TS and CTR5 primers ([5'-CCCTAA-3']$_5$, SEQ ID NO:20) are described below. Other primer pairs and reaction conditions can be utilized as is apparent to one of skill in the art. With the GeneAmp™ in situ PCR system 1000 and GeneAmp™ in situ PCR core kit (Perkin Elmer), 50 $\mu$l of reaction mix (10 mM Tris-HCl, 50 mM KCl, pH 8.3; 2.5 mM MgCl$_2$; 200 $\mu$M dNTPs; 1 $\mu$M TS and CTR5 primers; 10 U AmpliTaq™ DNA polymerase) is added to the sample heated to 70° C., sealed with a silicone gasket and clip (following the manufacturer's protocol, Perkin Elmer), and amplified for 30 cycles of 94° C./40 sec, 55° C./90 seconds. For direct detection of the amplified products, tagged dUTP or primers (tagged by fluorescent labels, radioisotope, biotin or digoxigenin, with a ratio of tagged dUTP to dTTP of 94 $\mu$M T-dUTP:106 $\mu$M dTTP) can be incorporated during the PCR amplification. After completion of the last PCR step, the sample is washed 3 times in wash buffer (4×SSC; 0.05% Tween 20) at 70° C., for 2 minutes.

To reduce background signals that can arise from direct incorporation of tagged dNTPs into cellular DNAs, prior to the in situ PCR amplification, samples can be pretreated with dNTPs and a DNA polymerase without the primers, optionally with a DNA ligase. The DNA polymerase, preferably Taq DNA polymerase, forms a complementary copy of any single-stranded regions in the cellular DNA and the ligase, preferably a thermostable ligase, eliminates any nicks in the resulting product. The addition of DNA polymerase in the amplification step is thus not required if the sample is pretreated with a thermostable DNA polymerase.

D. Signal detection

Fluorescent in situ hybridization (FISH) can be employed to identify telomerase positive cells in a mixed population of cells or tissues. After permeabilization of a tissue or cell sample fixed onto a microscopic glass slide, the nucleic acids are denatured by immersing the slide in 70% deionized formamide/2×SSC solution pre-warmed to 70°–74° C. for 2–3 minutes. The slide is transferred to ice-cold 70% EtOH, and then to 95% EtOH, and then to 100% EtOH (4 minutes in each solution). Labelled probe (e.g., 100–200 ng of a plasmid insert containing about 500 bp of 5'-TTAGGG-3' repeat sequence is used per slide. The probe can be labelled with biotin, digoxigenin, radioisotope, or a fluorescent tag. After labelling, the probe is dried, resuspended in 10 $\mu$l of 100% deionized formamide, denatured by incubation at 75° C. for 8 minutes, and immediately cooled on ice. To this, 10 $\mu$l of 2×hybridization buffer (4×SSC; 4×Denhardt's solution; 20% dextran sulfate; 100 mM Tris, pH 7.5) is added. The probe/hybridization mix (20 $\mu$l) is added to the fixed sample, overlayed with a coverslip, and the coverslip sealed with rubber cement or nail polish before incubating the sample at 37° C. for 8–48 hours. The coverslip is then removed and the sample is washed twice with 2×SSC/50% deionized formamide at 37° C., and then twice with 2×SSC at 37° C. (5 minutes per wash).

If the DNA probe is labelled with a fluorescent tag or radioisotope, the sample can be mounted in antifade solution (VectaShield™, VectaLab), or developed using a photographic emulsion, and viewed under a microscope. Digoxigenin-labelled probes are detected following the manufacturer's conditions using conjugated anti-digoxigenin antibodies (Boehringer Mannheim). If the probe is labelled with biotin, the slide can be blocked with 2×SSC/1% BSA for 10 minutes at room temperature, and then incubated in fluorescent conjugated avidin/2×SSC/1% BSA (final avidin concentration: 5 µg/ml) at room temperature for 1 hour. The slide can then be washed 5 minutes at room temperature in the following series: 4×SSC, 4×SSC/0.1% Triton X-100, 4×SSC, PN buffer (0.1M $Na_2HPO_4$; 0.1M $NaH_2PO_4$ and 0.1% Nonidet P40). The sample can be mounted in antifade and viewed under a microscope. For amplification of the signal, the slide is blocked in PNM buffer (PN buffer plus 5% [w/v] non-fat dried milk) at room temperature for 10 minutes, and incubated in a solution of biotinylated anti-avidin antibody (5 µg/ml) in PNM buffer at room temperature for 20 minutes. The slide is then washed in the four-step wash series described above, blocked again with PNM buffer, and incubated with fluorescently conjugated avidin (5 µg/ml) in PNM buffer at room temperature for 20 minutes. The slide is washed again by the four-step wash series, mounted in antifade and the result is viewed under a microscope.

It will be apparent to one of skill in the art that many variations of the in situ hybridization protocol described above can be applied in the methods of the invention. For example, a variation to the above in situ hybridization detection method involves primed-in situ labelling (PRINS; Koch, J., in "Nonradioactive in situ Hybridization Application Manual" (1992), Boehringer Mannheim, 31–33). Detection of telomere repeats by PRINS involves using an oligo-nucleotide probe specific for telomere repeats and chain elongation incorporating labelled nucleotides.

PRINS mixture (10 µl) of 5% (v/v) glycerol; 10 mM Tris-HCl, pH 8.3; 100 mM KCl; 0.05% (w/v) Tween 20; 0.75 mM EGTA; 2.5 mM $MgCl_2$; 0.4 µM return primer [e.g., $CTR_4$]; 200 µM dATP, dGTP, dCTP; 110 µM dTTP; and 90 µM labelled dUTP, is placed on the fixed, permeabilized sample, sealed with a coverslip, anchored with nail polish, overlayed with mineral oil, and incubated at 70° C. for 30 minutes to 3 hours. After completion of the PCR, the sample is washed 3 times in wash buffer (4×SSC; 0.05% Tween 20) heated to 70° C. for 2 minutes and the signal can be observed as described above.

To reduce the background signals that can arise from direct incorporation of fluorescent tags during the PCR amplification, indirect detection that involves PCR amplification using non-tagged dNTPs and unlabelled primers is used. In situ hybridization is then utilized to detect the PCR amplified product using a product-specific tagged hybridization probe as described above.

E. Elongation of in situ PCR product

In situ PCR can be improved by minimizing leakage of PCR amplified products from the cell. For this reason, the PCR product is typically larger than 200 bp, preferably larger than 500 bp, and more preferably larger than 700 bp. Alternatively, leakage of PCR products smaller than 200 bp from the cellular matrix can be prevented by incorporation of "bulky" dNTPs (e.g., a biotin-labelled dNTP, a fluorescent-labelled dNTP or a digoxigenin-labelled dUTP) into the PCR product or by incorporation of a product extension primer into the in situ PCR protocol. Illustrative primers for such a protocol are a primer that contains multiple copies (three to four) of a 6 bp repetitive incomplete (or mismatched) telomeric sequence (e.g., [5'-TTTCCC-3']$_{3-4}$) (SEQ ID NO:21 and SEQ ID NO:22) at its 5' end, followed by a sequence that is specific for the target, an appropriate return primer, and a third primer that contains incomplete repetitive sequences (e.g., [5'-TTTCCC-3']$_4$) (SEQ ID NO:22). These primers can be used to amplify the specific target by in situ PCR. The presence of the third primer elongates the PCR product due to its staggered-binding to the 3'-end of the target PCR product. The elongation of the PCR products can be further induced by decreasing the annealing temperature during the initial PCR condition.

For example, if the annealing temperature of the first primer to the target sequence is 60° C., the sample is initially amplified for 15–20 cycles of 94° C./45 seconds and 60° C./45 seconds, then amplified for 15–20 cycles of 94° C./45 seconds and 50° C./45 seconds. The lowered annealing temperature in the second PCR step favors staggered-binding of the third primer to the repetitive sequences and thus the generation of elongated PCR products. The resulting elongated PCR products are less prone to leakage through the cellular matrix, thus resulting in improved signal retention in in situ PCR analysis.

EXAMPLE 6

Preparation of TRAP Reaction Beads

This Example illustrates the use of a wax barrier to separate the PCR return primer from other reagents to ensure that the return primer is accessible to the DNA polymerase, and any extended telomerase substrates, during the TRAP assay only at temperatures that ensure highly specific nucleic-acid base pairing and so reduces nonspecific primer extension and primer-dimer formation.

A primer solution (e.g., ACT; 5–10 ng/µg) with a trace amount of bromophenol blue is mixed with clean sterile glass beads (e.g., ~300 micron in diameter, acid-washed, commercially available from Sigma). The bromophenol blue can be added to monitor possible leakage through the wax barrier prior to thermal cycling. While the addition of dye for this purpose is in no way required for practice of the present invention, dye addition can be a convenient method for monitoring the integrity of a manufacturing process. The mix is dried until the beads are coated with an appropriate amount of dried primers (See Example 2), and the primer-coated beads are then mixed with hot molten wax. While vigorously mixing, the bead/wax mixture is dispensed onto a clean surface by pipetting and then allowed to solidify. One bead droplet is added to a PCR tube and used in a TRAP assay using the conditions described in Example 2.

Alternatively, the primer solution (e.g., ACT; 5–10 ng/µl) is mixed with glass beads (~1000 micron in diameter). An aliquot of hot molten wax (~5 µl) is placed into a plug mold having a covered lower surface and is left to harden. The bead is placed on top of the hardened wax layer and a second aliquot of hot molten wax (~5 µl) is placed into the mold over the bead, and allowed to harden. The cover of the lower surface is removed and the finished plug is pushed through the mold. One plug per TRAP assay is used instead of the conventional reaction tube, and the TRAP assay is conducted as described above in Example 2.

It will be apparent to those of skill in the art that many variations of these two embodiments are possible, such as the use of various primers and surfaces other than glass beads.

EXAMPLE 7

Wax-Free/Hot-Start-Free TRAP Assay

There are various formats for reducing primer-dimer artifacts other than the use of a wax barrier illustrated in Example 6, such as choice of reaction conditions. For example, and without limitation, the addition of about 5% dimethylsulfoxide (DMSO) to the TRAP buffer can reduce the formation of primer-dimer artifacts. The addition of glycerol in combination with DMSO compensates for the potential enzyme destabilization caused by DMSO. Thus, addition of about 5% glycerol to samples in TRAP buffer containing about 5% DMSO can be beneficial where enzyme stability is critical.

Appropriate primer design can also be employed to reduce primer-dimer formation. An illustrative primer is the ACX return primer (5'-GCGCGG[CTTACC]$_3$CTAACC-3', SEQ ID NO:4) which is a chimeric oligonucleotide that has the anchor sequence of the ACT primer (5'-GCGCGG-3') (SEQ ID NO:2) at its 5' end followed by a CX primer-based sequence that contains mismatches (5'-[CTTACC]$_3$CTAACC-3', SEQ ID NO:23) in 3 of 4 complementary telomeric repeats (5'-TAACCC-3'). TRAP assays were performed essentially as described in Example 2 using 293 extracts with either TS and ACX, or TS and ACT, in the presence of about 5% DMSO, using cold start conditions (i.e., without a wax barrier) and the products were separated on a 15% polyacrylamide gel. Control samples lacked input extract, and one set of control samples included a synthetic telomerase product (TSR8; 5'-AATCCGTCGAGCAGAGTTAG[CGGTTAG]$_7$-3' SEQ ID NO:19). Results with no input 293 extract or with synthetic product showed that the TS and ACT combination resulted in primer-dimer artifacts, whereas no primer-dimer artifacts were observed with TS and ACX primers.

To test the robustness of the ACX primer, an attempt was made to induce primer-dimer artifact formation with TS primer by incubating the TRAP assay mixture including TS and ACX on ice without a wax-barrier, and then initiating a PCR amplification in a non-preheated thermocycler block. The combination of TS and ACX primers consistently showed no primer-dimer artifact formations and had no detrimental effect on the efficiency of the TRAP reaction. Furthermore, TS and ACX primers were equally resistant to primer-dimer formation in the absence of DMSO. Therefore, the utilization of the TS and ACX primers in the TRAP assay can replace the wax-barrier methodology for the TRAP assay, thus making the analysis, manufacturing, and the performance of the TRAP assay components more reproducible, simple, and reliable. However, as will be apparent to the artisan, such primers can be used in various embodiments, including the wax-barrier methodology.

EXAMPLE 8

TRAP Product Detection by TaqMan™ Detection System

The method involves detecting extended telomerase substrates using the non-radioactive TaqMan™ detection system (Perkin Elmer) modified for use in the TRAP assay. A TaqMan™ probe that possesses both a fluorescent reporter dye tag and a quencher dye tag is incorporated into the primer extension reaction (e.g., PCR amplification). Although there is no precise limitations on the positions of these tags, it will be apparent to one of ordinary skill in the art that particular positions may be preferable to others; for example, the tags are preferably positioned 6–8 nucleotides apart.

An illustrative probe for use in this detection system comprises repetitive CTR (5'-CCCTAA-3') sequences. In a convenient format, the CTR probe and return primer (e.g., ACT) are both separated by a wax barrier for use in the hot-start methodology described in Example 2.

A second illustrative probe that comprises a sequence complementary to the telomerase substrate does not compete with either the TS or ACT primers, and thus does not result in primer-dimer formation. Although the artisan may be concerned that the formation of a duplex between such a probe with the TS primer can potentially decrease PCR efficiency, telomerase was demonstrated to recognize and extend such double-stranded substrates in an assay using PCR detection as described below.

A duplex DNA (GTSI-1) was constructed by hybridizing an equal amount of M2A telomerase substrate primer (modified TS: 5'-GCCCAATCCGTCGAGCAGAGTTAG-3'; SEQ ID NO:25) with its complementary sequence CM2A (5'-CTAACTCTGCTCGACGGATTGGGC-3'; SEQ ID NO:26). GTSI-1 was used in a TRAP assay with the return primer, HKC (a variation of the anchored CTR primer: 5'-CTCGGTACCAAGCTTCTAACCCTAACCCTAACC-3'; SEQ ID NO:27), and 293 extract, under cold-start conditions (i.e., no wax barrier) essentially as described in Example 2. The TRAP product was observed with this primer combination and was demonstrated to be RNase sensitive thus demonstrating the utility of probes that are complementary to the telomerase substrate in detecting telomerase activity. Thus, CM2A can be used as a TaqMan™ probe.

Modifications to the probe design are easily accomplished by those of ordinary skill in the art. For example, a probe can be used which contains a sequence complementary to the 3' region of the TS primer, followed by a CTR sequence (e.g., 5'-AACCCTAACCCTAACTCTGCT-3'; SEQ ID NO:7) with a reporter dye at is 5' end and a quencher dye internal to the 5' end, preferably about 7 nucleotides internal to the 5' end. This primer specifically hybridizes to the junction between the TS primer and the telomeric repeat sequence thereby reducing any competitive effect that may occur with the ACT-probe and TS-probe duplex formation. A probe containing the TS sequence and at least one TTAGGG repeat can also be used in the TaqMan™ detection system, preferably using the hot start methodology of Example 2.

EXAMPLE 9

Multiplex Electrophoretic Separator (MES)

The Multiplex Electrophoretic Separator (MES) is an apparatus that allows for analysis of multiple samples simultaneously. The apparatus comprises two electroconducting sheets (e.g., copper) with the same configuration as a multiwell plate. The two sheets act as electrodes (FIG. 1). A 15% non-denaturing polyacrylamide gel was prepared in a bottomless multiwell plate temporarily sealed to allow polymerization of the gel. After removal of the seal, the multiplex gel unit was placed equidistant from the two electrodes, and the complete apparatus was submerged in electrophoresis buffer (e.g., 0.5×TBE; 0.045M Tris-borate, 0.001M EDTA).

For illustration of a method using the apparatus, radioactively labelled TS primer was used as a substrate in a TRAP assay using 10-fold serial dilutions of 293 cell extracts (from $10^5$–$10^1$ cell equivalents) essentially as described in Example 2. As controls, 5-fold serial dilutions of the synthetic product TSR8 from 10 fmol–16 amol (see Example 7) were also included. Each assay/dilution was prepared in triplicate.

After the TRAP reaction, each sample was loaded onto the top of a well of the MES and an electric field was applied across the gel. After separation of the products from non-incorporated dNTPs and primers, the gel was washed with water and the product inside the gel detected by means of a PHOSPHORIMAGER™ apparatus (Molecular Dynamics). In this illustrative embodiment, a commercially available microtiter plate was used. As the plate material had not been optimized for the assay, scattering of the radioactivity by the plastic walls of the MES gel unit caused a haziness in the signal. However, this apparatus can be used to distinguish negative samples (RNase controls and no extract) from positive samples, and telomerase activity could be detected in samples diluted 10000-fold with linear quantitation over an extensive range, up to 1000-fold under the selected reaction conditions. As is apparent to the artisan, various materials can be used in the MES, and assay conditions can be varied in accordance with this specification.

EXAMPLE 10

Detection of Telomerase Activity with TRAP-SYBR Green

The TRAP assay is carried out on telomerase samples essentially as described above in Example 4, typically in a total volume of 50 µl, but using unlabelled primer. Typically, PCR parameters for the TRAP-SYBR Green assay are 22–35 cycles of a two step program, i.e., 94° C./30 seconds and 60° C./30 seconds. After electrophoresis, the gel is stained with SYBR Green to visualize products.

In an alternative embodiment, to reduce background, the reaction mixture is treated with 25 µl of 0.3M acetate buffer, pH 4.5 containing 500 ng RNase and 10 units of S1 nuclease and incubated at 37° C. for 15 minutes to digest excess primers and RNA in the telomerase extract. As an alternative to electrophoresis, aliquots (50 µl) of a 1:2000 dilution of SYBR Green dye (Molecular Probes) can be added to wells of a microtiter plate, and 50 µl aliquots of the digested TRAP assay are mixed with the dye for measurement of telomerase activity. The double-stranded DNA/dye complex is detected with a fluorometric plate reader using an excitation wavelength of 497 nm and an emission wavelength of 520 nm. Such a non-radioactive telomerase assay is simple, inexpensive and, if desired, has the potential for high through-put screening in a clinical reference laboratory or for screening compounds for telomerase inhibitory activity, and still allows easy quantitation of DNA products in a sample.

EXAMPLE 11

Single-cell Telomerase Repeat Amplification Protocol (STRAP)

To illustrate the sensitivity of the TRAP assay, this Example describes a method for detecting telomerase activity in a single cell. Single cells can be obtained by various means, such as by serial dilution or using a fluorescence activated cell sorter (FACS) sorting either whole cell lines or specifically marked populations of cells. The latter method is illustrated in the present Example. The cells are marked with fluorescently labelled or labelable antibodies, which antibodies recognize a specific marker. The marker can differentiate cells of different life spans, function or are differentially expressed.

Cells were sorted into 25 µl of preparatory buffer containing 20 mM Tris-HCl (pH 8.3), 1.5 mM $MgCl_2$, 63 mM KCl, 1 mM EGTA, 1 mg/mL BSA, 0.5% Tween 20, 50 mM dNTPs, 100 ng of TS oligonucleotide, and DEPC-treated water. The buffer was placed in 8-tube microtiter format PCR strips. The concentration of Tween 20 was sufficient to lyse the cell membrane. The reaction time used in this Example, although not limiting, was 60 minutes at 30° C. The incubation was performed in the block of a microtiter format Perkin Elmer 9600 thermal cycler. One can also use a heat block or water bath.

Following incubation, an additional 25 µl of amplification buffer was added to each reaction tube. The amplification buffer contained the same ingredients noted above except the TS oligonucleotide was replaced by 100 ng of gamma end-labelled return primer, ACX. The ACX oligonucleotide was labelled in a reaction containing T4 polynucleotide kinase (NEB), 10×PNK buffer (NEB), and a ratio of 100 µCi of 3000 Ci/mmol γ-$^{32}$P ATP per 1 µg of ACX. T4 kinase was used at a ratio of 40 U per 1 µg of ACX and incubated at 37° C. for 30 minutes, followed by a heat treatment of 65° C. for 15 minutes to inactivate the kinase. Taq DNA polymerase (2 U; Boehringer Mannheim) was added to the amplification buffer and amplification was performed in a Perkin Elmer 9600 thermal cycler for 32 cycles of 94° C., 30 seconds and 60° C., 30 seconds. Products were analyzed by electrophoresis in 0.6×TBE on 15% polyacrylamide non-denaturing gels. Those of skill in the art will recognize that the ratio of radioactive label to primer allows for the preparation of a primer with a high specific activity resulting in a strong signal from amplified products and detection of telomerase activity at the level of a single cell.

EXAMPLE 12

Method of Detecting Telomerase Activity from Body Fluids

This Example provides a non-invasive, simple method, particularly useful in a clinical setting, for collecting cells from body fluids for use in telomerase activity assays. For illustrative purposes, the method is described for collecting cells from the urogenitary tract; however, it should be noted that the method is not limited to use with urine, but can be applied to other body fluids, such as, saliva, phlegm, sputum, blood, fine needle aspirates of tumors (e.g., breast tumors, prostate tumors, or other tumor types where fine needle aspirates are used). Furthermore, it will be apparent to one of ordinary skill in the art that numerous other variations of the methods are possible.

(A) Sample preparation and storage
Method 1

1. Collect voided urine (30–40 ml) in a 50 ml centrifuge tube.
2. Centrifuge at 1000 g for 15 minutes.
3. Carefully discard supernatant so that the pellet is not disturbed.
4. Resuspend pellet in 30 ml of PBS; repellet by centrifugation.
5. Resuspend pellet in 1 ml of PBS, transfer to a 1.5 ml centrifuge tube and repellet by centrifugation.
6. Establish cell count by using a Coulter counter or hemocytometer.
7. Carefully discard all supernatant.

One can freeze the cell pellet for shipping on dry ice or storage at −80° C. at this point, if desired.
Method 2

1. Collect voided urine (30–40 ml) in 50 ml centrifuge tube.
2. Add 100% glycerol to the collected urine to a final concentration of 20%, or add 100% DMSO to the collected urine to a final concentration of 10%.

One can keep the treated sample on dry ice for shipping or store at −80° C. at this point, if desired. Before use, the sample is treated as described in steps 2 to 7 of Method 1.

Method 3

1. Collect voided urine and establish cell count by using a Coulter counter or hemocytometer.
2. Filter voided urine (30≧40 ml) through a 0.45 micron filter.
3. Pass 10 ml of PBS through the same filter.

One can seal the filter in a sterile plastic bag, and ship on dry ice or store at −80° C. at this point, if desired.

(B) Extraction Procedures

Extraction procedures for pelleted cells.

1. Add 20 µl of CHAPS lysis buffer to $1 \times 10^6$ cells or less. If the cell number is not known, add a volume of lysis buffer equal to the packed-cell volume.
2. Follow the standard CHAPS extraction method described in Example 1 to obtain an extract.

Extraction Procedure for cells collected on a filter

1. Cut the filter into small pieces (~2 mm square).
2. Resuspend the filter pieces in CHAPS lysis buffer (20 µl of CHAPS lysis buffer for $1 \times 10^6$ cells), making sure that the volume of lysis buffer is equal to or greater than the packed volume of the filter pieces.
3. Follow the standard CHAPS extraction method described in Example 1 to obtain an extract.

(C) TRAP analysis of the urine-derived extract

Extracts (2–5 µl) are used in a standard TRAP assay with 30–35 PCR cycles as described in Example 2. Sensitivity can be increased by addition of one or more radioactively-labelled dNTPs, in addition to the end-labelled primers. The presence of telomerase activity is correlated with the presence of cancer cells in the urine sample and a diagnostic for urogenitary cancer.

As described above, the method can be used for any body fluid or fine needle aspirate, thus allowing the presence of telomerase activity to be correlated with the presence of cancer cells in the fluid or aspirate and a diagnostic for the particular cancer, e.g., lung cancer when sputum or phlegm is the tested fluid, and breast cancer when a fine needle aspirate of breast or other (e.g., prostate) tissue is tested.

EXAMPLE 13

TRAP Assay Reagents and Kit Formats

In this Example, a variety of reagents and kit formats are provided for the practitioner's convenience in carrying out the TRAP assay. In part A, a CHAPS lysis buffer is described. In part B, a TRAP internal control is described. In part C, various kit formats are described. It will be apparent that variation in the reagents and kits are possible depending on their intended use.

(A) CHAPS Lysis Buffer

A preferred CHAPS lysis buffer has the composition: 10 mM Tris-Cl, pH 7.5; 1 mM MgCl$_2$; 1 mM EGTA; 0.1 mM benzamidine; 5 mM β-mercaptoethanol; 0.5% CHAPS; 10% glycerol. Addition of KCl to a concentration of 1 mM, and an increase in the concentration of CHAPS detergent to 3%, in the CHAPS lysis buffer, increases the efficiency of the telomerase extraction 2–5 fold. Thus, a modified CHAPS lysis buffer for use in the TRAP assay contains 10 mM Tris-Cl, pH 7.5; 1 mM MgCl$_2$; 1 mM EGTA; 0.1 mM 4-(2-aminoethyl)-benzenesulfonylfluoride (AEBSF) or benzamidine; 5 mM β-mercaptoethanol; 0.5–3% CHAPS; and 1 mM Cl.

B TRAP internal control (TSNT)

The internal control TSNT, having the sequence 5'-AATCCGTCGAGCAGAGTTAAAAGGCCGAGAAG-CGAT-3' (SEQ ID NO:5), can be amplified by the TS telomerase substrate primer and a return primer, NT, having the sequence 5'-ATCGCTTCTCGGCCTTTT-3' (SEQ ID NO:6). The NT is not a substrate for telomerase. This control can be incorporated into a TRAP assay kit, optionally included in the 10×TRAP buffer (at a concentration of ~0.002 amol/µl) or in the primer mixture (0.01 amol/µl), and results in a TRAP product of 36 bp. The above primer pairs and internal control are merely illustrative; any primer pair and complementary control can be substituted therefor.

(C) TRAP Kit Formats

A wide variety of kits and components can be prepared according to the present invention, depending upon the intended user of the kit and the particular needs of the user. Illustrative kits for performing the TRAP assay are provided below. Such kits can be prepared from readily available materials and reagents and can be easily varied as is apparent to one of ordinary skill in the art.

In its simplest form, a kit comprises a telomerase substrate with or without instructions. In a further embodiment, a kit comprises a telomerase substrate and a return primer. In another embodiment, a kit comprises a telomerase substrate, a return primer and one or more buffers. The buffer can be, for example, a cell lysis buffer, end-labelling buffer or TRAP reaction buffer. The TRAP reaction buffer can optionally contain a control reagent, e.g., control oligonucleotides such as TSNT or TSR8, although such control reagents can be provided separately within the kit. The kit can further comprise positive cell extracts or cell pellets, negative cell extracts or pellets, reaction vessels, water, nucleotides, labels, or enzymes. The positive cell pellet can be 293 cells, HeLa cells or any other telomerase positive cell pellet or a panel of multiple cell types with varying amounts of telomerase activity. The kits can be provided with or without instructions. Preferably, instructions describe how to use the reagents in the assay method described in Example 4.

A preferred kit comprises the following reagents:

1. CHAPS lysis buffer (10 mM Tris-Cl, pH 7.5; 1 mM MgCl$_2$; 1 mM EGTA;
   0.1 mM Benzamidine; 5 mM β-mercaptoethanol; 0.5% CHAPS; 10% glycerol)
2. 10×TRAP reaction buffer (200 mM Tris-Cl, pH 8.3; 15 mM MgCl$_2$; 630 mM KCl; 0.5% Tween 20; 10 mM EGTA; 1 mg/ml BSA)
3. 50×dNTP mix (2.5 mM dATP, 2.5 mM dGTP, 2.5 mM dCTP, and 2.5 mM dTTP)
4. TS primer (0.1 µl)
5. Water (PCR grade; protease, DNase and RNase-free)
6. Positive control cell pellet ($10^6$ cells) or a panel of multiple cell types with varying amount of telomerase activity.

It will be apparent to one of ordinary skill in the art that a particular reagent concentration can be varied without detrimental effect, and further such variation in a stock solution may or may not reflect variation in the concentration of the reagent when in use.

A particularly preferred kit format further comprises a TRAP primer mix (e.g., ACX 0.1 µg/l; NT 0.1 µg/µl; TSNT 0.01 amol/µl) optionally with a quantitation standard (e.g., TSR8; 0.1 amol/µl).

In another embodiment the kit comprises CHAPS lysis buffer, 10×TRAP reaction buffer containing TSNT (0.002 amol/µl), 50×dNTP mix, TS primer (1 µg/µl), water (PCR grade; protease, DNase and RNase-free), a positive control cell pellet ($10^6$ cells) or a panel of multiple cell types with varying amount of telomerase activity, TRAP reaction tubes (0.1 μg ACT sealed with wax), Taq DNA polymerase (5 U/μl), optionally provided with 10×End-labelling buffer (100 mM Tris-OAc; 100 mM MgOAc; 500 mM KOAc), polynucleotide kinase (1 U/μl) and gel loading dye. Alternatively, the TRAP reaction tubes described above can be replaced with ACX primer (50×concentration, 0.1 μg/μl).

EXAMPLE 14

Telomerase Activity Detection by Branched DNA (bDNA) Probes

This Example illustrates the use of bDNA probes for detecting telomerase activity in a microtiter plate format. The use of bDNA probes in the methods of the invention are not limited to such a format, as the bDNA probes can be used in various ways, for example, in in situ detection of telomerase extension products. For the convenience of the practitioner, it should be noted that reagents for bDNA are available from Chiron Corp., CA., and oligonucleotides are available from Synthetic Genetics Corp., CA. Alternatively, nucleic acids can be linked to a solid surface using conventional attachment chemistry techniques, for example, via amide or ester linkages.

In one format, multi-well plates are prepared with the telomerASE substrate oligonucleotide, TS, (5'-AATCCGTCGAGCAGAGTT-3'; SEQ ID NO:3) bound to the plate at its 5' end. Cell extracts are prepared as described in Example 1. Telomerase buffer (100 μl; 20 mM Tris-Cl pH 8.3, 1.5 mM $MgCl_2$, 63 mM KCl, 0.05% Tween 20, 1 mM EGTA, 0.1 mg/ml BSA, 50 μM dNTPs) and 5 μl of CHAPS telomerase cell extract are added to the TS-bound microtiter plates and incubated for 30 minutes to 2 hours at 30° C. The reaction mix is then removed from the well and the well washed twice with 200 μl of 1×SSC (8.76 g/l NaCl, 4.41 g/l Na citrate, pH7) at room temperature. Fifty microliters of 1×SSC containing ~15 pmol of bDNA probe specific for the telomeric repeats (i.e., containing at least three repeats of 5'-(CCCTAA)-3'; SEQ ID NO:17) is then added to the well and incubated at ~55° C. for 30 minutes with gentle shaking. The bDNA probe mix is then removed from the well and the well washed twice with 200 μl of 0.1×SSC at 37° C. Fifty microliters of 1×SSC containing ~50 pmol of a secondary probe (e.g., an FITC-labelled 18-mer oligonucleotide) specific for the branched arms of the bDNA is then added to the well (U.S. Pat. No.: 5,124,246. Urdea, 1994) and incubated at ~55° C. for 30 minutes with gentle shaking. The solution is removed from the well and the well washed twice with 0.1×SSC at 37° C. before adding 200 μl of 0.1×SSC. Telomerase products are then detected by an appropriate means, for example, by employing a fluorescent plate reader when a fluorescent label is used.

A further illustrative format involves the immobilization of the telomerase substrate to a microtiter plate using complementary nucleic acids. Telomerase buffer (100 μl; 20 mM Tris-Cl pH 8.3, 1.5 mM $MgCl_2$, 63 mM KCl, 0.05% Tween 20, 1 mM EGTA, 0.1 mg/ml BSA, 50 μM dNTPs;) containing 15 pmol of TS primer is added to a sterile standard microtiter plate together with 5 μl of CHAPS telomerase cell extract (the amount of extract can be as high as 50% of the total reaction volume). The plate is incubated for 30 minutes to 2 hours at 30° C., after which the solution is transferred to a second microtiter plate having complementary TS primers bound by their 5' ends (e.g., one or more repeats of 5'-AACTCTGCTCGACGGATT; SEQ ID NO:24). The second plate is then incubated at ~55° C. for 30 minutes with gentle shaking before removing the solution from the well and washing the well twice with 200 μl of 1×SSC at 37° C. Fifty microliters of 1×SSC containing ~15 pmol of bDNA probe specific for the telomeric repeats is then added to the well. The plate is incubated at ~55° C. for 30 minutes with gentle shaking after which the solution is removed from the well. The well is then washed twice with 200 μl of 0.1×SSC at 37° C. Fifty microliters of 1×SSC containing ~50 pmol of rhodamine-labelled secondary probe specific for the branched arms of the bDNA is then added to the well. After incubating the plate at ~55° C. for 30 minutes with gentle shaking, the solution is removed and the well is then washed twice with 0.1×SSC at 37° C. The fluorescence can be conveniently detected using a fluorescent plate reader after addition of 200 μl of 0.1×SSC although other methods exist, such as direct visualization.

Various modifications of these formats are possible, such as, performing the telomerase reaction described above in a complementary TS-bound microtiter plate, thus eliminating the transfer step, immobilizing after the telomerase extension reaction with nucleic acids complementary to telomerase repeats or immobilizing prior to the telomerase reaction using nucleic acids complementary to the telomerase substrate. Furthermore, a wide variety of labels can be used other than a fluorescent label and the signal from such labels can be increased by probing the bDNA specific for the telomerase extension product with a second bDNA probe specific for the first bDNA branches, in which case the second bDNA probe is labelled (directly or indirectly with a further probe).

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:

(A) LENGTH: 24 base pairs
                (B) TYPE: nucleic acid
                (C) STRANDEDNESS: single
                (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:1:

CCCTTACCCT TACCCTTACC CTAA 24

(2) INFORMATION FOR SEQ ID NO:2:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:2:

GCGCGGCTAA CCCTAACCCT AACC 24

(2) INFORMATION FOR SEQ ID NO:3:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:3:

AATCCGTCGA GCAGAGTT 18

(2) INFORMATION FOR SEQ ID NO:4:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:4:

GCGCGGCTTA CCCTTACCCT TACCCTAACC 30

(2) INFORMATION FOR SEQ ID NO:5:

(i) SEQUENCE CHARACTERISTICS:
                (A) LENGTH: 36 base pairs
                (B) TYPE: nucleic acid
                (C) STRANDEDNESS: single
                (D) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:5:

AATCCGTCGA GCAGAGTTAA AAGGCCGAGA AGCGAT        36

( 2 ) INFORMATION FOR SEQ ID NO:6:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:6:

ATCGCTTCTC GGCCTTTT        18

( 2 ) INFORMATION FOR SEQ ID NO:7:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:7:

AACCCTAACC CTAACTCTGC T        21

( 2 ) INFORMATION FOR SEQ ID NO:8:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: synthetic ( i i i ) HYPOTHETICAL: NO ( i v ) ANTI-SENSE: NO ( x i ) SEQUENCE DESCRIPTION: SEQ ID NO:8:

CCTAACCCTA ACCCCACTAT GCT        23

( 2 ) INFORMATION FOR SEQ ID NO:9:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:9:

CCTAACCCTA ACCCTGTATA TGCT 24

( 2 ) INFORMATION FOR SEQ ID NO:10:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:10:

GCGCGGCTTA CCCTTACCCT TACCCTAACC AAT 33

( 2 ) INFORMATION FOR SEQ ID NO:11:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

CCCAATCCGT CGAGCAGAGT TAG 23

( 2 ) INFORMATION FOR SEQ ID NO:12:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:12:

TAACTCTGCT CGACGGATTC CC 22

( 2 ) INFORMATION FOR SEQ ID NO:13:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:13:

GGGTAACCCT AACCCTAACC C                                                                          21

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:14:

GGTTAGGGTT AGGGTTAAA                                                                              19

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:15:

GTTAGGGTTA GGGTTAGG                                                                               18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic ( i i i ) HYPOTHETICAL: NO ( i v ) ANTI-SENSE: NO ( x i ) SEQUENCE DESCRIPTION: SEQ ID NO:16:

TTAGGGTTAG GGTTAGGG                                                                               18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:17:

CCCTAACCCT AACCCTAA                                                                               18

( 2 ) INFORMATION FOR SEQ ID NO:18:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:18:

CCCTAACCCT AACCCTAACC CTAA                                                                 24

( 2 ) INFORMATION FOR SEQ ID NO:19:

( i ) SEQUENCE CHARACTERISTICS:
           ( A ) LENGTH: 62 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:19:

AATCCGTCGA GCAGAGTTAG GGTTAGGGTT AGGGTTAGGG TTAGGGTTAG GGTTAGGGTT AG    62

( 2 ) INFORMATION FOR SEQ ID NO:20:

( i ) SEQUENCE CHARACTERISTICS:
           ( A ) LENGTH: 30 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:20:

CCCTAACCCT AACCCTAACC CTAACCCTAA                                        30

( 2 ) INFORMATION FOR SEQ ID NO:21:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:21:

TTTCCCTTTC CCTTTCCC                                                                        18

( 2 ) INFORMATION FOR SEQ ID NO:22:

( i ) SEQUENCE CHARACTERISTICS:
           ( A ) LENGTH: 24 base pairs (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:22:

TTTCCCTTTC CCTTTCCCTT TCCC                                                24

(2) INFORMATION FOR SEQ ID NO:23:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:23:

CTTACCCTTA CCCTTACCCT AACC                                                24

(2) INFORMATION FOR SEQ ID NO:24:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:24:

AACTCTGCTC GACGGATT                                                       18

(2) INFORMATION FOR SEQ ID NO:25:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:25:

GCCCAATCCG TCGAGCAGAG TTAG                                                24

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (  i  i  ) MOLECULE TYPE: DNA (synthetic)

( i i i ) HYPOTHETICAL: NO (  i v ) ANTI-SENSE: NO ( x i ) SEQUENCE DESCRIPTION: SEQ ID NO:26:

C T A A C T C T G C    T C G A C G G A T T    G G G C                                                   2 4

( 2 ) INFORMATION FOR SEQ ID NO:27:

( i ) SEQUENCE CHARACTERISTICS:
                ( A ) LENGTH: 33 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:27:

C T C G G T A C C A    A G C T T C T A A C    C C T A A C C C T A    A C C                               3 3

What is claimed is:

1. A method for determining whether a cell sample contains telomerase activity, said method comprising the steps of:
  (a) collecting a cell sample;
  (b) incubating said cell sample in a reaction mixture comprising an exogenous telomerase substrate under conditions such that telomerase can catalyze extension of said telomerase substrate by addition of telomeric repeat sequences;
  (c) replicating said extended telomerase substrate; and
  (d) correlating presence of telomerase activity in said cell sample with presence of said extended telomerase substrate and absence of telomerase activity in said cell sample with absence of said extended telomerase substrate.

2. The method of claim 1, wherein said telomerase substrate lacks a telomeric repeat sequence and said replicating step comprises adding to said reaction mixture a template-dependent DNA polymerase and a primer that will hybridize to said extended telomerase substrate and be extended by said DNA polymerase to form a complementary copy of said extended telomerase substrate if an extended telomerase substrate is present in said reaction mixture.

3. The method of claim 2, wherein said replicating step further comprises the steps of:
  (1) heating said reaction mixture to denature duplex DNA molecules; and
  (2) cooling said reaction mixture to a temperature at which complementary nucleic acids can hybridize and said primer can extend if extended telomerase substrates are present.

4. The method of claim 3, wherein said heating and cooling steps are repeated at least 5 times, and said primer is present in amounts sufficient for the formation of extended primers during each cooling step.

5. The method of claim 3, wherein said DNA polymerase is a thermostable template-dependent DNA polymerase and said primer is extended by addition of nucleotides to said primer by said DNA polymerase.

6. The method of claim 2, wherein said telomerase substrate lacking a telomeric repeat sequence is 5'-AATCCGTCGAGCAGAGTT-3' (SEQ ID NO:3).

7. The method of claim 2, wherein said reaction mixture comprises a labelled telomerase substrate or a labelled primer.

8. The method of claim 7, wherein said primer comprises a fluorescent label and a quenching dye and further comprises non-complementary sequences at the 3'-end of said primer.

9. The method of claim 2, wherein said primer comprises a non-telomeric repeat sequence at a 5'-end of said primer.

10. The method of claim 2, wherein said primer is 5'-CCCTTACCCTTACCCTTACCCTAA-3' (SEQ ID NO: 1), 5'-GCGCGGCTAACCCTAACCCTAACC-3' (SEQ ID NO:2) or 5'-GCGCGGCTTACCCTTACCCTTACCCTAACC-3' (SEQ ID NO:4).

11. The method of claim 2, further comprising adding to said reaction mixture an oligonucleotide that will hybridize to said extended telomerase substrate, or said complementary copy at a site 3' to said primer, said oligonucleotide comprising a fluorescent label and a quenching dye.

12. The method of claim 2, wherein said replicating step further comprises adding to said reaction mixture an oligonucleotide control for primer extension.

13. The method of claim 2, wherein the presence of extended telomerase substrate is detected by incorporating a label into said complementary copy of said extended telomerase substrate, said label selected from the group consisting of a radioactive label, a fluorescent label, a phosphorescent label, a chromogen, an enzyme, an enzyme substrate, biotin, avidin and digoxigenin.

14. The method of claim 2, wherein the presence of extended telomerase substrate is detected using a branched DNA probe.

15. The method of claim 1, wherein said replicating step comprises adding to said reaction mixture a thermostable template-dependent DNA ligase, an oligonucleotide ligomer that will hybridize to said extended telomerase substrate, and a primer that will hybridize to said extended telomerase substrate and be extended by ligation of said oligonucleotide ligomer to said primer by said DNA ligase if an extended telomerase substrate is present in said cell sample.

16. The method of claim 1, wherein said cell sample is a human cell sample.

17. A method for determining whether a cell sample contains telomerase activity, said method comprising the steps of:
   (a) incubating a cell sample or a cell extract in a reaction mixture comprising a telomerase substrate and a buffer in which telomerase can catalyze extension of said telomerase substrate by addition of telomeric repeat sequences;
   (b) adding to said reaction mixture a template-dependent RNA polymerase that recognizes a promoter sequence operably linked to said telomerase substrate;
   (c) allowing said RNA polymerase to form an RNA copy of said extended telomerase substrate if an extended telomerase substrate is present in said reaction mixture; and
   (d) correlating presence of telomerase activity in said cell sample with presence of RNA copies of said extended telomerase substrate and absence of telomerase activity in said cell sample with absence of said RNA copies.

18. The method of claim 17, further comprising adding to said reaction mixture a template-dependent DNA polymerase and a primer sufficiently complementary to a telomeric repeat to hybridize specifically thereto and said primer is extended by addition of nucleotides to said primer by said DNA polymerase.

19. The method of claim 18, wherein said primer comprises at least one telomeric repeat sequence.

20. The method of claim 17, wherein said RNA polymerase recognizes a single-stranded nucleic acid substrate.

21. The method of claim 20, wherein said RNA polymerase is an N4 RNA polymerase.

22. The method of claim 17, wherein said RNA polymerase is selected from the group consisting of an SP6 RNA polymerase, a T7 RNA polymerase and a T3 RNA polymerase.

23. The method of claim 17, wherein said cell extract is prepared by lysing cells in said cell sample in a buffer comprising a non-ionic or zwitterionic detergent.

24. A method for determining whether a cell sample contains telomerase activity, said method comprising the steps of:
   (a) incubating a cell sample or a cell extract in a reaction mixture comprising a telomerase substrate lacking a telomeric repeat sequence and a buffer in which telomerase can catalyze extension of said telomerase substrate by addition of telomeric repeat sequences;
   (b) immobilizing said telomerase substrate;
   (c) adding to said reaction mixture a probe comprising a sequence sufficiently complementary to the extended telomerase substrate to hybridize specifically thereto under conditions such that if an extended telomerase substrate is present in said reaction mixture, said probe will hybridize to said extended telomerase substrate; and
   (d) correlating presence of telomerase activity in said cell sample with presence of said probe hybridized to extended telomerase substrate and absence of telomerase activity in said cell sample with absence of hybridization of said probe.

25. The method of claim 24, wherein said cell extract is prepared by lysing cells in said cell sample in a buffer comprising a non-ionic or zwitterionic detergent.

26. The method of claim 24, wherein said probe is a branched DNA probe.

27. The method of claim 24, wherein said probe is a labelled probe.

28. The method of claim 24, wherein said hybridized probe is detected using a nucleic acid dye.

29. The method of claim 24, wherein said probe comprises a sequence complementary to a telomeric repeat sequence.

30. The method of claim 24, wherein said probe is a biotinylated probe and said probe is detected by tyramide signal amplification.

31. The method of claim 24, wherein said telomerase substrate is immobilized after said incubating step with said cell extract. substrate.

32. The method of claim 31, wherein telomeric repeat sequences added to said telomerase substrate during said incubating step are immobilized and said probe comprises a sequence complementary to said telomerase substrate.

33. The method of claim 31, wherein said probe is complementary to said telomeric repeat sequences.

34. A kit for detecting telomerase activity, said kit comprising:
   (a) a telomerase substrate; and
   (b) a primer comprising a sequence complementary to a telomeric repeat sequence.

35. The kit of claim 34 wherein said kit further comprises a cell lysis buffer and an assay buffer.

36. The kit of claim 34, wherein said kit further comprises an oligonucleotide control for primer extension and a cell pellet.

37. The kit of claim 34, wherein said kit further comprises an oligonucleotide control for primer extension, and a cell sample or a cell extract.

38. The kit of claim 34, wherein said primer is selected from the group consisting of 5'-CCCTTACCCTTACCCTTACCCTAA-3'(SEQ ID NO: 1), 5'-GCGCG GCTAACCCTAACCCTAACC-3' (SEQ ID NO:2) and 5'-GCGCGGCTTACCCTTA CCCTTACCCTAACC-3'(SEQ ID NO:4).

39. The kit of claim 34, wherein said telomerase substrate is 5'-AATCCGTCGAGCAGAGTT-3' (SEQ ID NO:3), said primer is 5'-GCGCGGCTTA CCCTTACCCTTACCCTAACC-3' (SEQ ID NO:4) and said kit further comprises a CHAPS lysis buffer, 10×TRAP reaction buffer, a stock solution of dATP, dGTP, CHAPS lysis buffer, 10×TRAP reaction buffer, a stock solution of dATP, dGTP, dCTP and dTTP, 5'-AATCCGTCGAGCAGAGTTAAAAGGCCGAGAAG-CGAT-3' (SEQ ID NO:5), 5'-TAACATCGCTTCTCGGCCTTT-3' (SEQ ID NO:6), 5'-AATCCGTCGAGCAGAGTTAGGGTTAGGGTTAGG-GTTAGGGTTAGGGTTAGGG TTAGGGTTAG-3'(SEQ ID NO: 19), water and a positive control cell pellet.

40. A purified preparation of an oligonucleotide wherein said oligonucleotide is 5'-AATCC GTCGAGCAGAGTTAAAAGGCCGAGAAGCGAT-3' (SEQ ID NO:5) or 5'-TAAC ATCGCTTCTCGGCCTTTT-3' (SEQ ID NO:6).

41. The kit of claim 34, wherein said telomerase substrate lacks a telomeric repeat sequence.

42. A method for determining whether a cell sample contains telomerase activity, said method comprising the steps of:
   (a) collecting a cell sample or a cell extract;
   (b) incubating said cell sample or said cell extract in a reaction mixture comprising a telomerase substrate under conditions such that telomerase can catalyze extension of said telomerase substrate by addition of telomeric repeat sequences;

(c) amplifying said extended telomerase substrate, wherein said amplifying is mediated by a template-dependent ligase, a template-dependent RNA polymerase or a branched nucleic acid probe; and (d) correlating presence of telomerase activity in said cell sample with presence of said extended telomerase substrate and absence of telomerase activity in said cell sample with absence of said extended telomerase substrate.

43. The method of claim 42, wherein said telomerase substrate lacks a telomeric repeat sequence.

44. The method of claim 42, wherein said amplifying step further comprises adding to said reaction mixture a template-dependent DNA polymerase and a primer that will hybridize to said extended telomerase substrate and be extended by said DNA polymerase to form a complementary copy of said extended telomerase substrate if an extended telomerase substrate is present in said reaction mixture.

* * * * *